US009271953B2

(12) United States Patent
Driscoll

(10) Patent No.: US 9,271,953 B2
(45) Date of Patent: Mar. 1, 2016

(54) METHODS FOR CORRECTION OF ORGAN DYSFUNCTION

(71) Applicant: Genetic Disease Investigators, LLC, Roanoke, TX (US)

(72) Inventor: Diana Driscoll, Roanoke, TX (US)

(73) Assignee: GENETIC DISEASE INVESTIGATORS, LLC, Roanoke, TX (US)

( * ) Notice: Subject to any disclaimer, the term of this patent is extended or adjusted under 35 U.S.C. 154(b) by 0 days.

(21) Appl. No.: 14/209,717

(22) Filed: Mar. 13, 2014

(65) Prior Publication Data

US 2014/0274957 A1 Sep. 18, 2014

Related U.S. Application Data

(60) Provisional application No. 61/779,131, filed on Mar. 13, 2013, provisional application No. 61/856,938, filed on Jul. 22, 2013, provisional application No. 61/900,697, filed on Nov. 6, 2013.

(51) Int. Cl.
| | |
|---|---|
| *A61K 31/205* | (2006.01) |
| *A61K 31/221* | (2006.01) |
| *A61K 31/685* | (2006.01) |
| *A61K 31/4748* | (2006.01) |
| *A61K 31/51* | (2006.01) |
| *A61K 31/465* | (2006.01) |
| *A61K 45/06* | (2006.01) |
| *A61K 31/14* | (2006.01) |
| *A61K 33/06* | (2006.01) |
| *A61K 9/00* | (2006.01) |

(52) U.S. Cl.
CPC .............. *A61K 31/221* (2013.01); *A61K 31/14* (2013.01); *A61K 31/465* (2013.01); *A61K 31/4748* (2013.01); *A61K 31/51* (2013.01); *A61K 31/685* (2013.01); *A61K 33/06* (2013.01); *A61K 45/06* (2013.01); *A61K 9/0014* (2013.01); *A61K 9/0031* (2013.01); *A61K 9/0034* (2013.01); *A61K 31/205* (2013.01)

(58) Field of Classification Search
CPC ........................ A61K 31/205; A61K 31/221
USPC ........................................................ 514/556
See application file for complete search history.

(56) References Cited

U.S. PATENT DOCUMENTS

| | | |
|---|---|---|
| 6,537,969 B1 | 3/2003 | Blass |
| 6,964,969 B2 | 11/2005 | McCleary |
| 7,599,736 B2 | 10/2009 | DiLorenzo |
| 7,705,016 B2 | 4/2010 | Rossetti et al. |
| 8,349,376 B1 | 1/2013 | Bezzek |
| 2011/0015154 A1 | 1/2011 | Kellerman et al. |
| 2011/0034376 A1 | 2/2011 | Lubbers et al. |

FOREIGN PATENT DOCUMENTS

WO    2014160423 A1    10/2014

OTHER PUBLICATIONS

Australian Patent Office (ISA), International Search Report and Written Opinion for PCT/US2014/026559 dated Jun. 30, 2014, 8 pp.
Abell, et al., "Treatment of gastroparesis: a multidisciplinary clinical review." Neurogastroenterol Motil, (2006) 18 (4):263-283.
Agarwal, et al., "Postural orthostatic tachycardia syndrome." Postgrad Med J. (2007) 83(981): 478-480.
Bachofen, et al. "The role of nitric oxide." Rheumatology. (2006) 45:3:7-9.
Beaumont, et al., "Reduced Cardiac Vagal Modulation Impacts on Cognitive Performance in Chronic Fatigue Syndrome." PloS ONE. (Nov. 14, 2012), 7(11):e9518.
Bennett, R.M., "Adult Growth Hormone Deficiency in Patients with Fibromyalgia." Curr Rheumatol Rep. (2002), 4(4):306-12.
Bernardi, et al., "Widespread cardiovascular autonomic dysfunction in primary amyloidosis: does spontaneous hyperventilation have a compensatory role against postural hypotension?" Heart. (Dec. 2002), 88(6):615-621.
Bohora, S., "Joint hypermobility syndrome and dysautonomia: expanding spectrum of Disease presentation and manifestation." Indian Pacing Electrophysiol J. (published online Apr. 1, 2010), 10(4): 158-161.
Busha, et al., "Termination of inspiration by phasedependent respiratory vagal feedback in awake normal humans." J Appl Physiol. (published Sep. 1, 2002) 93:903-910.
Castori, Marco, "Ehlers-Danlos syndrome, hypermobility type: an underdiagnosed hereditary connective tissue disorder with mucocutaneous, articular, and systemic manifestations." Dermatol. Published online Nov. 22, 2012: 751768.
Dartt, Darlene A., "Neural Regulation of Lacrimal Gland Secretory Processes: Relevance in Dry Eye Diseases." Progress in Retinal and Eye Research. (May 2009) 28:155-177.
Eccles, et al., Brain structure and joint hypermobility: relevance to the expression of psychiatric symptoms. The British Journal of Psychiatry. (2012) 200(6):508-509.
Fin, et al., "Mild autonomic dysfunction in primary Sjogren's syndrome: a controlled study." Arthritis Research & Therapy. (published Mar. 7, 2008) 10:R31.
Fischer, et al., "Sex and menopausal status influence human dietary requirements for the nutrient choline." Am J Clin Nutr. (2007) 85(5):1275-1285.
Gibbons, et al., "Structural and Functional Small Fiber Abnormalities in the Neuropathic Postural Tachycardia Syndrome." PLoS ONE (Dec. 2013) 8(12): e84716.
Hakim, et al., "Non-musculoskeletal symptoms in joint hypermobility syndrome. Indirect evidence for autonomic dysfunction?" Rheumatology. (2004), vol. 43, Issue 9:1194-1195.

(Continued)

*Primary Examiner* — Kevin E Weddington
(74) *Attorney, Agent, or Firm* — Edwin S. Flores; Daniel J. Chalker; Chalker Flores, LLP

(57) ABSTRACT

The present invention includes compositions and methods for treating certain conditions, the composition comprising a choline compound; a cholinesterase inhibitor; and Acetyl-L-Carnitine, wherein the composition is used to treat at least one of autonomic dysfunctions or vascular diseases.

12 Claims, 5 Drawing Sheets

(56) References Cited

OTHER PUBLICATIONS

Ho, et al., "Drug discovery from Chinese medicine against neurodegeneration in Alzheimer's and vascular dementia." Chin Med. (2011) 6:15.
Itier, et al. (Aug. 2001). "Neuronal nicotinic receptors: from protein structure to function." FEBS Letters, (first published online Jul. 25, 2001), 504 (3): 118-25.
Janse Van Rensburg, et al., "Autonomic impairment in rheumatoid arthritis." International Journal of Rheumatic Diseases. (2012), 15(4):419-26.
Kanjwal, et al., "Autonomic dysfunction presenting as postural orthostatic tachycardia syndrome in patients with multiple sclerosis." Int J Med Sci. (2010), 7(2): 62-67.
Kanjwal, et al., "Clinical presentation and management of patients with hyperadrenergic postural orthostatic tachycardia syndrome. A single center experience." Cardiol J. (2011), 18(5):527-31.
Malik, Marek, "Heart Rate Variability; Standards of Measurement, Physiological Interpretation, and Clinical Use." Circulation. (1996) 93:1043-1065.
Mehedint, et al. "Maternal dietary choline deficiency alters angiogenesis in fetal mouse hippocampus." PNAS. (Jul. 20, 2010). 107(29):12834-12839.
Milewicz, et al. "Vascular Ehlers-Danlos Syndrome: Exploring the Role of Inflammation in Arterial Disease." Circulation: Cardiovascular Genetics. (Feb. 2014) 7:5-7.
Parnetti, L, et al. "Cholinergic precursors in the treatment of cognitive impairment of vascular origin: Ineffective approaches or need for re-evaluation?" Journal of the Neurological Sciences, (2007), 257 (1-2):264-9.
Plioplys A.V., Plioplys S., "Serum levels of carnitine in chronic fatigue syndrome: clinical correlates." Neuropsychobiology (1995) 32:132-138.
Robertson, et al. "Primer on the Autonomic Nervous System." second edition, (New York: Academic Press) 2004, pp. 1-386.
Timothy, C.O., "Effect of 0.5% glucose intake on the tear production of normoglycemic emmetropic Nigerians." JNOA (2009) 15:12-15.
Tombul, et al., "Impaired heart rate variability as a marker of cardiovascular autonomic dysfunction in multiple sclerosis", Acta Neurol Belg. (2011), 111(2):116-20.
Traviesa, D.C., "Magnesium deficiency: a possible cause of thiamine refractoriness in Wernicke-Korsakoff encephalopathy." Journal of Neurology, Neurosurgery, and Psychiatry. (1974) 37:959-962.
Virmani, et al., "Acetyl-L-Carnitine modulates TP53 and IL1 gene expression induced by 3-NPA evoked toxicity in PC12 cells." Curr Neuropharmacol. (2011) 9(1): 195-199.
Wang, et al., "Deficiency of Nicotinic Acetylcholine Receptor B4 Subunit Causes Autonomic Cardiac and Intestinal Dysfunction." Molecular Pharmacology. (2003), vol. 63, No. 3; 574-580.
Zarate, et al., "Unexplained gastrointestinal symptoms and joint hypermobility: is connective tissue the missing link?" Neurogastroenterology & Motility. (2010), 22(3)252-e78.
Zeisel, Steven H., "Choline: Critical role during fetal development and dietary requirements in Adults." Annu Rev Nutr. (2006) 26:229-250.

METHODS FOR CORRECTION OF ORGAN DYSFUNCTION

CROSS-REFERENCE TO RELATED APPLICATIONS

This application claims priority to U.S. Provisional Application Ser. No. 61/779,131, filed Mar. 13, 2013, U.S. Provisional Application Ser. No. 61/856,938, filed Jul. 22, 2013, 2013, and U.S. Provisional Application Ser. No. 61/900,697, filed Nov. 6, 2013, the entire contents of which are incorporated herein by reference.

TECHNICAL FIELD OF THE INVENTION

The present invention relates in general to the field of prevention and treatment of conditions associated with autonomic dysfunction and their commonly found co-morbid conditions including vascular disorders, immunological disorders and organ dysfunction and more particularly, to methods and composition for the prevention and treatment of the same.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with the treatment and prevention of autonomic dysfunctions.

One such method of treatment is taught in U.S. Pat. No. 7,599,736, issued to DiLorenzo, entitled "Method and apparatus for neuromodulation and physiologic modulation for the treatment of metabolic and neuropsychiatric disease." Briefly, this inventor teaches an apparatus and method for physiological modulation, including neural and gastrointestinal modulation, for the purposes of treating several disorders, including obesity, depression, epilepsy, and diabetes. The method and apparatus includes a chronically implanted neural and neuromuscular modulator, used to modulate the afferent neurons of the sympathetic nervous system to induce satiety, including neuromuscular stimulation of the stomach to effect baseline and intermittent smooth muscle contraction to increase gastric intraluminal pressure, stimulation of sympathetic afferent fibers, including those in the sympathetic trunk, splanchnic nerves, and greater curvature of the stomach.

United States Patent Application No. 20110034376, filed by Lubbers, et al., is entitled, "Use of Lipid-Rich Nutrition for the Treatment of Post-Operative Ileus." Briefly, the invention is directed to the use of a lipid-rich nutrition for the manufacture of a composition for the prevention and/or treatment of post-operative ileus. In peritoneal lavage fluid, the lipid fraction was said to inhibit IL-6 and TNF-alpha levels, wherein the lipid fraction prevents influx of neutrophils in the intestinal muscularis following intestinal manipulation.

Finally, United States Patent Application No. 20070093434, filed by Rossetti, et al., is entitled "Regulation of food intake and glucose production by modulation of long-chain fatty acyl-Co-A levels in the hypothalamus." Briefly, the invention is directed to methods of reducing food intake and glucose production in a mammal, or restoring hepatic autoregulation are provided. The methods involve increasing long-chain fatty acyl-Co-A (LC-CoA) levels in the hypothalamus, or stimulating efferent fibers in the hepatic branch of the vagus nerve.

SUMMARY OF THE INVENTION

In one embodiment, the present invention includes a composition comprising: a choline compound; a cholinesterase inhibitor; and Acetyl-L-Carnitine, wherein the composition is used to treat at least one of autonomic dysfunctions or vascular diseases. In one aspect, the composition treats or prevents autonomic dysfunction (dysautonomia, non-familial dysautonomia, partial autoimmune autonomic neuropathy, idiopathic autonomic neuropathy, neurocardiogenic syncope). In another aspect, the composition treats or prevents multiple organ dysfunction (constipation, gastroparesis, idiopathic gastrointestinal dysmotility, low gastric acid production, ileocecal valve dysfunction ("ileus"), breathing difficulties, low gall bladder ejection fractions, biliary dyskinesia, acalculous gall bladder disease, Sphincter of Oddi dysfunction, low cholecystokinin ("CCK") production, poor kidney function, non-alcoholic steatohepatitis (or "NASH"), or non-alcoholic fatty liver disease). In another aspect, the composition treats at least one of a genetic disorder or treats or prevents an acquired disorder of collagen (Ehlers-Danlos syndrome, Marfan's syndrome, Loeys-Dietz syndrome, Stickler syndrome, fibrillary disorders, elastin disorders, Joint Hypermobility Syndrome). In another aspect, the composition treats or prevents at least one of chronic infectious or fatigue syndromes (Chronic Fatigue Syndrome, Myalgic Encephalomylitis, Chronic Lyme disease, fibromyalgia or chronic pain associated with low growth hormone levels). In another aspect, the composition treats or prevents autoimmune disorders or multiple sclerosis. In another aspect, the composition treats or prevents a vascular disease and a rheumatological disease. In another aspect, the composition treats or prevents dry eyes, xerostomia (dry mouth), vascular disorders, poor nitric oxide production, endocrine disorders (including low growth hormone production), chronic fungal infections, or hallucinations. In another aspect, the composition treats or prevents dry eyes. In another aspect, the composition treats or prevents dry mouth. In another aspect, the composition treats or prevents visual snow. In another aspect, the composition prevents or restores vascular endothelial health as determined by decreased thrombosis, vascular abnormalities, or livido reticularis. In another aspect, the composition comprises: a choline compound selected from at least one of choline at 100 mg to 1,000 mg, lecithin at 100 mg to 3 grams, or L-alpha glycerylphosphorylcholine at 30 mg to 2,400 mg; 75 mcg to 300 mcg of the cholinesterase inhibitor is huperzine A; and 50 mg to 600 mg of Acetyl-L-Carnitine. In another aspect, the composition further comprises Thiamin. In another aspect, the composition further comprises Magnesium. In another aspect, the composition comprises per dose: a choline compound selected from at least one of choline at 100 mg to 1,000 mg, lecithin at 100 mg to 3 grams, or L-alpha glycerylphosphorylcholine at 30 mg to 2,400 mg; 75 mcg of huperzine A; 150 mg of Acetyl-L-Carnitine; and optionally 30 mg Thiamin and 30 mg Magnesium. In another aspect, the range per dose is 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300, of the choline compound. In another aspect, the range per dose is 75, 80, 90, 100, 125, 150, 175, 200, 225, 250, 275, 300, 75 to 300, 80 to 275, 90 to 250, 100 to 225, 125 to 200, 150 to 175 mcg of huperzine A. In another aspect, the range per dose is 50, 75, 80, 90, 100, 125, 150, 175, 200, 225, 250, 275, 300, 325, 350, 375, 400, 425, 450, 475, 500, 525, 550, 575, 600, 50 to 600, 75 to 600, 80 to 575, 90 to 550, 100 to 525, 125 to 500, 150 to 475, 175 to 450, 200 to 425, 225 to 400, 250 to 375, 275 to 350, 300 to 325 Acetyl-L-Carnitine. In another aspect, the range per dose is 10, 20, 30, 40, 50, 60 mg Thiamin. In another aspect, the range per dose is 0.3, 0.5, 0.75, 1.0, 5, 10, 15, 20, 25, 30, 40, 50, 60, 70, 80, 90, 100 mg Magnesium. In another aspect, the composition is adapted to be administered prenatally, orally, intravenously, intraperitoneally, intranasally, intrapulmonary, subcutaneously, intracutaneously, or intramuscularly.

In another embodiment, the present invention includes a composition consisting essentially of: 30 to 2,400 mg of at least one of choline, lecithin, or L-alpha glycerylphosphorylcholine; 75-300 mcg of huperzine A; 50 to 600 mg of Acetyl-L-Carnitine; and optionally including at least one of 10-180 mg Thiamin or Magnesium.

In another embodiment, the present invention includes a composition consisting of: 30 to 2,400 mg of at least one of choline, lecithin, or L-alpha glycerylphosphorylcholine; 75 mcg-300 mcg of huperzine A; 50 to 600 mg of Acetyl-L-Carnitine; and optionally including at least one of 10-180 mg Thiamin or Magnesium.

In yet another embodiment, the present invention includes a method of treating a autonomic dysfunctions or vascular diseases in a subject, comprising administering to a subject in need thereof an effective amount of a composition comprising a choline compound; a cholinesterase inhibitor and Acetyl-L-Carnitine. In one aspect, the composition treats or prevents autonomic dysfunction (dysautonomia, non-familial dysautonomia, partial autoimmune autonomic neuropathy, idiopathic autonomic neuropathy, neurocardiogenic syncope). In another aspect, the composition treats or prevents multiple organ dysfunction (constipation, gastroparesis, idiopathic gastrointestinal dysmotility, low gastric acid production, ileocecal valve dysfunction ("ileus"), breathing difficulties, low gall bladder ejection fractions, biliary dyskinesia, acalculous gall bladder disease, Sphincter of Oddi dysfunction, low cholecystokinin ("CCK") production, poor kidney function, non-alcoholic steatohepatitis (or "NASH"), or non-alcoholic fatty liver disease). In another aspect, the composition treats at least one of a genetic disorder or treats or prevents an acquired disorder of collagen (Ehlers-Danlos syndrome, Marfan's syndrome, Loeys-Dietz syndrome, Stickler syndrome, fibrillary disorders, elastin disorders, Joint Hypermobility Syndrome). In another aspect, the composition treats or prevents at least one of chronic infectious or fatigue syndromes (Chronic Fatigue Syndrome, Myalgic Encephalomyelitis, Chronic Lyme disease, fibromyalgia or chronic pain associated with low growth hormone levels). In another aspect, the composition treats or prevents autoimmune disorders or multiple sclerosis. In another aspect, the composition treats or prevents a vascular disease and a rheumatological disease. In another aspect, the composition treats or prevents dry eyes, xerostomia (dry mouth), vascular disorders, poor nitric oxide production, endocrine disorders (including low growth hormone production), chronic fungal infections, or hallucinations. In another aspect, the composition treats or prevents dry eyes. In another aspect, the composition treats or prevents dry mouth. In another aspect, the composition treats or prevents visual snow. In another aspect, the composition prevents or restores vascular endothelial health as determined by decreased thrombosis, vascular abnormalities, or livido reticularis. In another aspect, the composition comprises: a choline compound selected from at least one of choline at 100 mg to 1,000 mg, lecithin at 100 mg to 3 grams, or L-alpha glycerylphosphorylcholine at 30 mg to 2,400 mg; 75 mcg to 300 mcg of the cholinesterase inhibitor is huperzine A; and 50 mg to 600 mg of Acetyl-L-Carnitine. In another aspect, the composition further comprises Thiamin. In another aspect, the composition further comprises Magnesium. In another aspect, the composition comprises per dose: a choline compound selected from at least one of choline at 100 mg to 1,000 mg, lecithin at 100 mg to 3 grams, or L-alpha glycerylphosphorylcholine at 30 mg to 2,400 mg; 75 mcg of huperzine A; 150 mg of Acetyl-L-Carnitine; and optionally 30 mg Thiamin and 30 mg Magnesium. In another aspect, the range per dose is 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300, of the choline compound. In another aspect, the range per dose is 75, 80, 90, 100, 125, 150, 175, 200, 225, 250, 275, 300, 75 to 300, 80 to 275, 90 to 250, 100 to 225, 125 to 200, 150 to 175 mcg of huperzine A. In another aspect, the range per dose is 50, 75, 80, 90, 100, 125, 150, 175, 200, 225, 250, 275, 300, 325, 350, 375, 400, 425, 450, 475, 500, 525, 550, 575, 600, 50 to 600, 75 to 600, 80 to 575, 90 to 550, 100 to 525, 125 to 500, 150 to 475, 175 to 450, 200 to 425, 225 to 400, 250 to 375, 275 to 350, 300 to 325 Acetyl-L-Carnitine. In another aspect, the range per dose is 10, 20, 30, 40, 50, 60 mg Thiamin. In another aspect, the range per dose is 0.3, 0.5, 0.75, 1.0, 5, 10, 15, 20, 25, 30, 40, 50, 60, 70, 80, 90, 100 mg Magnesium. In another aspect, the composition is adapted to be administered prenatally, orally, intravenously, intraperitoneally, intranasally, intrapulmonary, subcutaneously, intracutaneously, or intramuscularly. In another aspect, method further comprises the steps of determining if the subject has an autonomic dysfunction as is seen in a genetic or an acquired disorder of collagen (Ehlers-Danlos syndrome, Marfan's syndrome, Loeys-Dietz syndrome, Stickler syndrome, fibrillary disorders, elastin disorders, Joint Hypermobility Syndrome) and providing to the subject during pregnancy the composition.

In one embodiment, the present invention includes a method of treating a medical condition, comprising: identifying a subject having the disease; and providing the patient with a medical composition that comprises: a choline compound selected from at least one of choline at 100 mg to 1,000 mg, lecithin at 100 mg to 3 grams, or L-alpha glycerylphosphorylcholine at 30 mg to 2,400 mg; 75 mcg to 300 mcg of huperzine A; 50 mg to 600 mg of Acetyl-L-Carnitine; and 10-180 mg Thiamin or Magnesium.

In another embodiment, the present invention includes a vaginal composition comprising: at least one of choline, lecithin, or L-alpha glycerylphosphorylcholine; huperzine A; and Acetyl-L-Carnitine, wherein the composition is adapted for vaginal administration and is provided in an amount sufficient to treat one or more autonomic dysfunctions or vascular diseases.

In yet another embodiment, the present invention includes a transdermal composition comprising: at least one of choline, lecithin, or L-alpha glycerylphosphorylcholine; huperzine A; and Acetyl-L-Carnitine, wherein the composition is adapted for transdermal administration and is provided in an amount sufficient to treat one or more autonomic dysfunctions or vascular diseases.

Yet another embodiment of the present invention includes a rectal composition comprising: at least one of choline, lecithin, or L-alpha glycerylphosphorylcholine; huperzine A; and Acetyl-L-Carnitine, wherein the composition is adapted for rectal administration and is provided in an amount sufficient to treat one or more autonomic dysfunctions or vascular diseases.

In one embodiment, the present invention includes a method for diagnosing post-ganglionic vagus nerve competency and effector organ function, comprising the steps of: identifying a patient suspected of having pre-ganglionic vagus nerve damage or symptoms thereof; providing the patient with an effective amount of transdermal, rectal or vaginal suppository, or subcutaneous nicotine; and determining the response of an effector organ, wherein if the effector organ functions following exposure to the nicotine, then the patient can be treated with a composition comprising a choline compound; a cholinesterase inhibitor; and Acetyl-L-Carnitine. In one aspect, the effector organ is selected from at least one of bowel, Sphincter of Oddi, or Ileocecal valve. In another aspect, the nicotine is used so long as tolerable. In another aspect, the nicotine treats constipation or gastroparesis.

In one embodiment, the present invention includes a method for treating pre-ganglionic vagus nerve damage or symptoms thereof comprising the steps of: identifying a patient suspected of having pre-ganglionic vagus nerve damage or symptoms thereof; and providing the patient with an effective amount of transdermal, rectal or vaginal suppository, or subcutaneous nicotine sufficient to treat the pre-ganglionic vagus nerve damage or symptoms thereof. In one aspect, the pre-ganglionic vagus nerve damage or symptoms thereof is determined by dysfunction of an effector organ selected from at least one of bowel, Sphincter of Oddi, or Ileocecal valve. In another aspect, the nicotine is used so long as tolerable. In another aspect, the nicotine treats constipation or gastroparesis.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
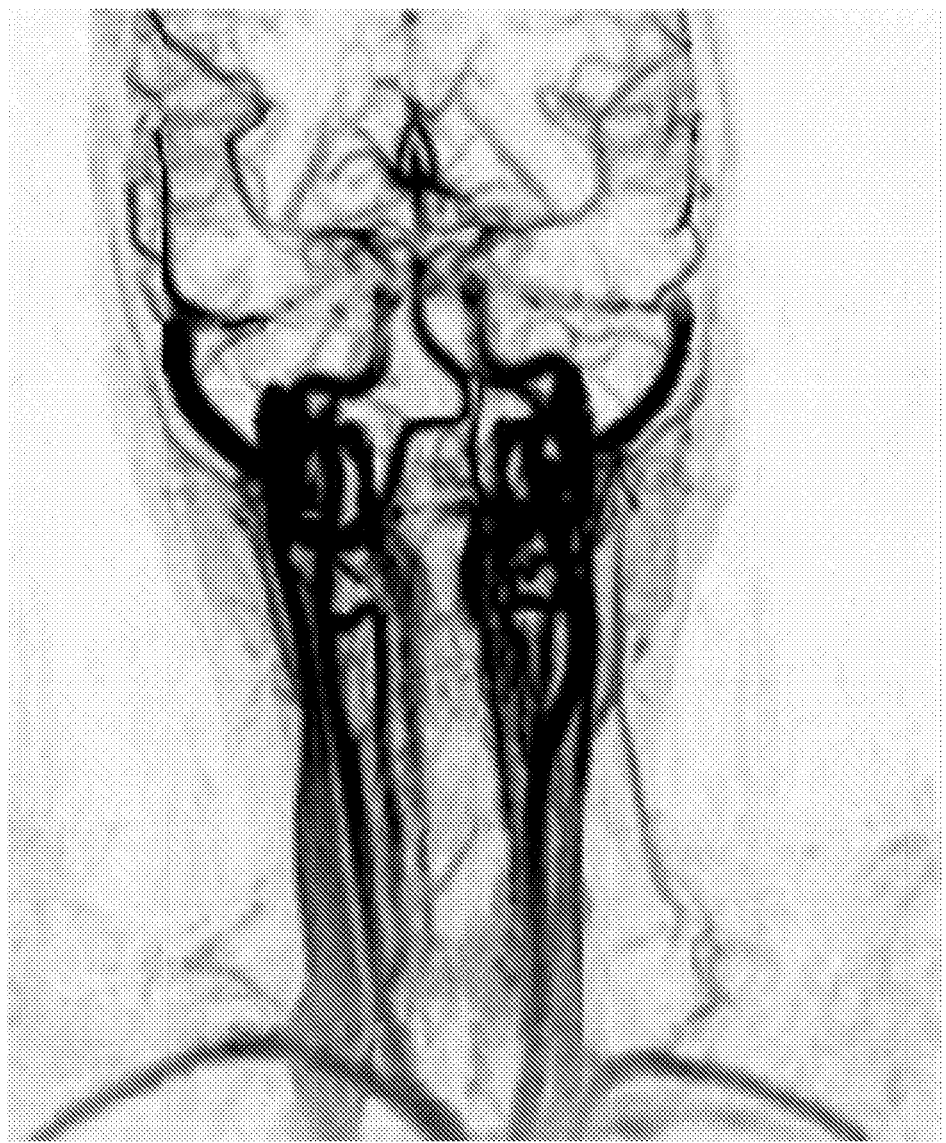
FIGS. 1A to 1C are examples of enlargement of internal jugular veins in patients with weak connective tissue (acquired and or genetic defects of connective tissue), Autonomic Dysfunction.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. N/A—not applicable.

The present inventor has recognized a need to treat and prevent autonomic dysfunction (dysautonomia, non-familial dysautonomia, partial autoimmune autonomic neuropathy, idiopathic autonomic neuropathy, neurocardiogenic syncope) and its associated conditions, as is often seen in patients with genetic and/or acquired disorders of collagen (which may include Ehlers-Danlos syndrome, Marfan's syndrome, Loeys-Dietz syndrome, Stickler syndrome, fibrillary disorders, elastin disorders, Joint Hypermobility Syndrome), chronic infectious and/or fatigue syndromes (which may include Chronic Fatigue Syndrome, Myalgic Encephalomyelitis, Chronic Lyme disease, fibromyalgia), autoimmune disorders (which may include multiple sclerosis), a vascular disease and a rheumatological disease. Autonomic dysfunction is a state of malfunction of the autonomic nervous system (ANS). The autonomic nervous system controls a number of functions in the body, such as heart rate, blood pressure, digestive tract peristalsis, and sweating, amongst others. Such dysfunction also presents with numerous co-morbid conditions, not apparently under autonomic control. The vast array of signs and symptoms of autonomic dysfunction have some common foundations, allowing for the prevention and treatment of this condition at its source (and preventing, reducing or reversing) the heretofore seemingly unrelated co-morbid conditions. Such co-morbid conditions include, but are not limited to multiple organ dysfunction (constipation, gastroparesis, idiopathic gastrointestinal dysmotility, low gastric acid production, ileocecal valve dysfunction ("ileus"), breathing difficulties, low gall bladder ejection fractions, biliary dyskinesia, acalculous gall bladder disease, Sphincter of Oddi dysfunction, low cholecystokinin ("CCK") production, poor kidney function, non-alcoholic steatohepatitis (or "NASH"), non-alcoholic fatty liver disease), dry eyes, xerostomia (dry mouth), vascular disorders, poor nitric oxide production, endocrine disorders (including low growth hormone production), chronic fungal infections, and hallucinations.

The present inventor also recognized that a need exists for the treatment of the root causes of autonomic dysfunction (as opposed to treating the individual symptoms) as is seen in genetic or acquired defects of collagen and in chronic infectious and/or fatigue syndromes, autoimmune disorders, in victims of physical and/or mental trauma (e.g., car accidents, whiplash, sport accidents, or other high impact trauma), in vascular disorders and rheumatological disease. These conditions result in a vast array of symptoms and signs involving organ dysfunction, vascular abnormalities including low nitric oxide production, visual snow, delusions, dry eyes, xerostomia (dry mouth), abnormal endocrine profiles (including low human growth hormone production) and motor dysfunction. The present invention is designed to simultaneously correct the underlying causes and contributing factors resulting in this vast array of symptoms and signs. Specifically, it has been found that the present invention provides almost immediate treatment for the symptoms (medical conditions) associated with the various medical diseases without the adverse side effects common to the use of the components of the composition at different doses. It has also been found that the composition functions in a manner superior to the individual components, and that symptomatic relief of gastrointestinal dysfunction (gastroparesis/constipation) is obtained almost immediately and in all cases within 2 to 3 hours, but no later than overnight. Surprisingly, it was also found that the listed doses avoided adverse side effects from the use of the same components alone and in different amounts. The only exception being the transdermal, vaginal suppository, or anal suppository form of nicotine, which effectively reverses some organ dysfunction, can be used as a diagnostic tool to verify that the organ is capable of responding, or can be used for short periods of time to assist with said organ function (ileocecal valve, gastroparesis/constipation).

The human body possesses numerous, often redundant systems for the production of essential neurotransmitters and enzymes, which allow the body to escape disease, organ dysfunction and neuronal damage. The present inventor has found that numerous chronic illnesses are due to the simultaneous loss of redundant pathways for the production, release and/or absorption of ingredients, neurotransmitters and enzymes required for health.

This patent includes compositions, methods of treatment and methods for preventing, diagnosing and treating autonomic dysfunction and its associated conditions and co-morbid presentations as is seen in non-neuropathic and neuropathic dysautonomia[34], autonomic dysfunction in Chronic Fatigue Syndrome ("CFS" or "M.E.", "Myalgic Encephalomyelitis"), "Postural Orthostatic Tachycardia Syndrome" or "POTS" and/or postural hypotension, hyperadrenergic "POTS", abnormal heart rate variability, Benign Joint Hypermobility Syndrome, Ehlers-Danlos syndrome and/or disorders of connective tissue, acquired and/or genetic defects (fibrin, elastin and/or collagen defects), Chronic Lyme Disease, fibromyalgia[33] and autoimmune disorders (which may include multiple sclerosis), mental trauma, a vascular disease and a rheumatological disease The organ dysfunction occurring in these conditions includes constipation, gastroparesis, idiopathic gastrointestinal dysmotility, low gastric acid production, ileocecal valve dysfunction, ileus, breathing difficulties, low gall bladder ejection fractions, biliary dyskinesia, acalculous gall bladder disease, Sphincter of Oddi dysfunction, low cholecystokinin ("CCK") production, poor kidney function, non-alcoholic steatohepatitis (or "NASH"), non-alcoholic fatty liver disease This composition corrects this organ dysfunction unless the organ is fibrotic, vessels to the organs are fibrotic or stenosed, or there is mechanical obstruction or blockage of the Sphincter of Oddi, pyloric valve, ileocecal valve or related structures.[35]

Although a variety of genetic, vascular and neurological processes contribute to the organ dysfunction, this composition is made to correct (and/or work around) the majority of defects present, most of which begin with vagus nerve compression or damage and involve a variety of genetic defects which result in symptoms and signs of acute anticholinergic poisoning and organ dysfunction, in addition to the numerous co-morbid presentations listed above.

Inadequate gastric acid secretion, gastroparesis, chronic constipation, ileocecal valve dysfunction, gall bladder dysfunction, Sphincter of Oddi dysfunction, and biliary dyskinesia, can all result in poorly digested food and bowel sitting in the gastrointestinal (G.I.) tract long enough to result in diverticulitis, mast cell activation of the mucocutaneous surfaces, colitis, allergies, Crohn's disease and other forms of G.I. inflammation and poor nutrient absorption. Ironically, and not obvious to those in the art, it was found by the present inventor that bowel disorders secondary to vascular nerve compression or damage to the preganglionic vagus nerve, eventually leads to organ dysfunction resulting in poor absorption of numerous other nutrients necessary to prevent signs and symptoms of dry eyes, dry mouth, delusions, motor dysfunctions, numbness and nystagmus. These symptoms and signs can be intermittent or wax and wane because they occur via unique and over-looked conditions such as nerve compression via venous dilation. The present inventor discovered that the symptoms and signs of the disorders could vary with patient position, blood volume and even sleeping posture, differentiating these conditions from the more easily understood disorders of malabsorption.

A majority of patients with these chronic syndromes resulting in such organ dysfunction are found to have numerous genetic defects of connective tissue (although approximately 90% are never diagnosed), which can result in weak vessels.[36] A unique method of diagnosing a cause of organ dysfunction presenting as chronic constipation, gastroparesis, idiopathic gastrointestinal dysmotility, low gastric acid secretion, ileocecal valve dysfunction ("ileus"), chronic vomiting, low gall bladder ejection fractions, biliary dyskinesia, acalculous gall bladder disease, Sphincter of Oddi dysfunction, non-alcoholic steatohepatitis, non-alcoholic fatty liver disease in addition to symptoms of heart palpitations, tachycardia and or bradycardia, difficulty breathing, abnormal (and often positional) variations in blood pressure comprises an fMRI or MRV of the internal jugular veins. (see FIG. 1). Often these patients will have a grossly enlarged internal jugular vein. When the abnormally enlarged internal jugular vein is found within the carotid sheath (also occupied by the carotid artery and the vagus nerve), compression of the vagus nerve results. (See FIG. 2). Such compression can render the vagus nerve incompetent or desensitized, but barring injury to the post-ganglionic portion of the nerve, successful stimulation of this portion of the nerve with a surge of agonists of nicotinic acetylcholine can cause proper response of the effector organ.[37]

Vagus nerve dysfunction is seen in patients with abnormal autonomic nervous system functioning as seen with abnormal heart rate variability tests, abnormal tilt table tests, abnormal sweat tests, and/or abnormal thermoregulatory testing. Vagus nerve dysfunction can be caused by vagus nerve compression by enlarged internal jugular veins (as demonstrated by FIGS. 1 and 2), vagus nerve malfunction or desensitization can be induced by injury (such as trauma, surgery, "nerve stretch" injuries, whiplash, vagotomy, spinal cord injury, compression by bones or abnormal calcium deposition or growths, abdominal, thoracic and/or heart surgery, "lap-band", gastric sleeve or other surgeries of the stomach) and opiate medications. Autoantibodies to autonomic receptors can also contribute to autonomic dysfunction. In most cases studied, organ dysfunction was found to be 'partial'—the organ may still function, but not consistently or reliably or completely (ileus would sometimes reverse, patients had some bowel movements, gall bladder ejection fractions were measurable, for example). This may be because most patients had one vagus nerve that was still functioning. Alternatively, some patients are found to have autoantibodies to acetylcholine receptors, but these are not sufficient to completely disable the receptors (patients do not exhibit multiple system atrophy or complete autonomic failure, for example). This indicates that the organ is capable of functioning, and by taking advantage of the partial or intermittent functionality of the organ, this composition is uniquely capable of stimulating the (undamaged) post-ganglionic nicotinic acetylcholine receptor, triggering normal organ response.

Vagus nerve dysfunction (and abnormal heart rate variability) is typically seen in patients with autonomic dysfunction as is often found in patients with genetic and/or acquired disorders of collagen, chronic infectious and/or fatigue syndromes, autoimmune disorders, vascular disease, and rheumatological diseases. This composition is designed to uniquely stimulate the post-ganglionic nicotinic acetylcholine receptors when damage to the vagus nerve is restricted to the pre-ganglionic portion of the nerve, resulting in the triggering of the effector organs and correction of organ dysfunction and numerous co-morbid conditions seen in autonomic dysfunction. Fortunately, the preganglionic vagus nerve is quite long (thus, unfortunately, susceptible to damage), but the post-ganglionic vagus nerve is short, and very close to the effector organ. This patent takes advantage of the often viable postganglionic vagus nerve in these conditions, and mimics the neuroreceptor release by a healthy preganglionic nerve, allowing for triggering of the post-ganglionic vagus nerve, and resulting in organ function.

Certain ingredients of the compound (a choline compound, an acetylcholinesterase inhibitor and Acetyl-L-Carnitine) have been used to reduce inflammation, to assist those suffering from metabolic insufficiencies, and for healthy memory and mental function, and numerous studies have been published involving cognition, dementia, age-related memory loss and neurodegeneration with these ingredients. (U.S. Pat. No. 6,537,969 B1, Patent No. US 2008/0213401). It is not intuitive or obvious that such compounds could be used effectively to stimulate the post-ganglionic nicotinic-acetylcholine portions of nerves located in the chest cavity or abdomen, however.

In one embodiment of the invention, transdermal (topical) application of nicotine, applied near the lower right-hand corner of the abdomen stimulates the post-ganglionic nicotinic acetylcholinergic receptor controlling the ileocecal valve, for example, allowing the valve to open. Oral nicotine, however, is ineffective at stimulating the post-ganglionic nicotinic acetylcholinergic nerves in the abdomen, yet it exposes the patient to the direct (and negative) effect on the cerebellum.[38] In numerous patients tested, oral physostigmine or Huperzine A (both inhibitors of acetylcholinesterase, and thus indirect stimulators of both nicotinic and muscarinic acetylcholine receptors) were not effective in stimulating organ function when the pre-ganglionic portion of the vagus nerve was damaged. It is clear that in addition to inhibitors of acetylcholinesterase, other ingredients are necessary to stimulate organ function in this patient population. In addition to the possibility of autoantibodies to acetylcholinergic receptors causing a need for more ingredients in the compound, genetic evaluations of the patients, and of the patients' mothers revealed abnormal polymorphisms that would require the addition of other ingredients in order for the compound to be effective (Data not included). It was only through extensive testing that the inventor was able to discover the proper range of oral ingredients which were effective in stimulating these post-ganglionic nerves. The inventor also uniquely incorporated adjustments in the formulas to take into account common genetic mutations in the study population—all without exceeding Upper Tolerable Limits of the ingredients This means that patients do not need to know their genetic history, nor even the extent of potential autoimmune involvement to get a positive response to the oral composition (without subjecting themselves to the generally intolerable side effects of transdermal nicotine, nor any possibility of "over-dosing" on any of these compounds, when taken as directed), another unique aspect of this compound.

The present invention can also be used to treat "visual snow" which is a transitory or persisting visual symptom where people see snow or television-like static in parts or the whole of their visual fields, especially against dark backgrounds ("type 1 visual snow"). It may also appear as a persistent and disturbing after-image ("type 2 visual snow"). It is much like camera noise in low light conditions, or static on a television. Although 65% of the 192 patients with connective tissue disorders and/or autonomic dysfunction (often seen in chronic fatigue syndromes) who provided symptom checklists (summarized hereinbelow) responded "yes" to the symptom of visual snow, this percentage dropped to 27% after ruling out migraine auras and vitreous floaters. This symptom is one of severe deficiency of one or more of the components of acetylcholine, for any reason.

Not intending to be bound by theory, and in no way a limitation of the present invention, the invention can be used as an acetylcholine agonist to stimulate production of the aqueous layer of the tear film (consisting of electrolytes, water and proteins), and thus be used as an effective treatment for chronic dry eyes. Dry eyes (xerophthalmia) is a common finding in autonomic dysfunction and in disorders of collagen biogenesis, including, but not limited to Ehlers-Danlos syndrome, Marfan's syndrome, Loeys-Dietz syndrome, Stickler syndrome, fibrillary disorders, elastin disorders, and Joint Hypermobility Syndrome. Such xerophthalmia was previously considered to be due to lagophthalmos due to defective collagen of the lids. In a survey of 192 patients with connective tissue disorders and/or autonomic dysfunction (often seen in chronic fatigue syndromes) 75% reported dry eye syndrome. Furthermore, it is understood that a normal rise in blood glucose occurring after ingestion of a carbohydrate-rich meal contributes to dry eyes for about 90 minutes.[39] Patients who suffer chronic organ dysfunction (and thus a poorly functioning gastrointestinal tract) often develop thiamin deficiencies, which may wax and wane. Because thiamin is needed for proper glucose utilization, when the patient experiences low thiamin, their levels of blood glucose often remain slightly elevated due to poor glucose utilization (much like their reduced ability to breakdown alcohol). When blood glucose levels remain on the upper end of normal ranges, dry eyes can be exacerbated. This compound corrects for the neurological causes of xerophthalmia, as long as the lacrimal gland is capable of functioning.

Not intending to be bound by theory, and in no way a limitation of the present invention, the invention (excluding nicotine) can be used as an acetylcholine agonist to stimulate production of gastric acid in the stomach (and thus help fight candida infections). In the cephalic phase of digestion, motor impulses are transmitted via the vagal nerve to the enteric ganglia which send neurons out to stimulate gastric acid secretion in the stomach glands. When gastric acid secretion is inadequate, digestion (and therefore nutrient absorption) is incomplete. Low gastric acid also encourages an alkaline environment where candida (and other fungi) can thrive. In a survey of 192 patients with autonomic dysfunction and/or connective tissue disorders, 70% reported having chronic candida infections (81% response rate).

Not intending to be bound by theory, and in no way a limitation of the present invention, the invention (excluding nicotine) can be used as an acetylcholine agonist to stimulate production of saliva by the salivary glands. Because parasympathetic stimulation leads to acetylcholine release onto the salivary acinar cells (stimulating the muscarinic receptors), this composition (excluding nicotine) can be used to increase the production of saliva. Interestingly, dry mouth (xerostomia) is a serious problem in many patients with connective tissue disorders, just as is the symptoms of xerophthalmia (dry eyes). Both can be reversed with the ingestion of this compound (excluding nicotine).[40]

Not intending to be bound by theory, and in no way a limitation of the present invention, the invention (excluding nicotine) can be used to stimulate production of human growth hormone, often found to be low in chronic pain syndromes, including disorders of connective tissue, "POTS", "Hyperadrenergic POTS" and fibromyalgia. Rather than treating the patients with exogenous growth hormone, the present invention instead treats the source of the low growth hormone levels (as measured via IGF-1). Growth hormone levels can then return to normal and dysregulation of the hypothalamic-pituitary-adrenal axis is normalized. Studies indicate that this patient population often suffers from low growth hormone levels, and benefits from increased growth hormone levels.[41][42] Studies in cattle provided evidence of the possibility of increasing growth hormone by increasing acetylcholine (in the presence of a cholinesterase inhibitor).[43] This composition uniquely corrects low growth hormone production by correcting the source of the low growth hormone levels in the human patient.

Magnesium deficiency is believed to be a possible cause of thiamin deficiency.[44] Because Magnesium is absorbed through the gastrointestinal tract, when normal intestinal function is restored with either topical nicotine (for short-term use) or ingestion or absorption of a choline compound, Acetyl-L-Carnitine and an acetylcholinesterase compound, absorption of magnesium can occur, which then contributes to proper absorption of thiamin.

A unique method for diagnosing pre-ganglionic vagus nerve dysfunction with no damage to post-ganglionic nicotinic acetylcholine receptors, involves stimulation of the post-ganglionic nicotinic acetylcholine receptors via the use of transdermal nicotine (3-21 mg nicotine) applied to the lower right-hand quadrant of the abdomen, near the location of the ileocecal valve. If the post-ganglionic nerve is capable of stimulation, nicotine (acting as a powerful agonist of nicotinic-acetylcholine) will reverse chronic constipation, gastroparesis, idiopathic gastrointestinal dysmotility, ileocecal valve dysfunction ("ileus"), and Sphincter of Oddi dysfunction (when the sphincter is not damaged or blocked) usually within hours. Such stimulation via nicotine can be used to check for organ response (the response of intestinal motility and/or opening of the ileocecal valve and/or Sphincter of Oddi occurs within hours). If this is effective, it verifies that stimulation of the nicotinic-acetylcholine post-ganglionic vagus nerve receptors is effective. Oral nicotine is not effective in stimulating the post-ganglionic nicotinic acetylcholine receptors sufficiently to result in organ function. It is not intuitive, obvious or previously discovered that the oral formulation consisting of a choline compound, a cholinesterase compound and Acetyl-L-Carnitine will stimulate the nicotinic-acetylcholine receptors, resulting in organ response. Treatment of organ dysfunction with this transdermal nicotine application can open the ileocecal valve and encourage G.I. motility, but it is not successfully used on a chronic basis because of side effects. The transdermal nicotine application can be used as a diagnostic tool to verify functioning of the post-ganglionic nerve and the effector organ, and it can be utilized for short-term use in patients who do not respond with dermatographia and/or skin irritation or welting (intolerance of the patch). Most patients in this affected population find frequent use of such a patch unacceptable because of activation of numerous cells which release histamine—these patients demonstrate dermatographia prior to use of the nicotine patch, and risk side effects ranging from local skin irritation to systemic anaphylaxis. In a survey of 192 patients with autonomic dysfunction and/or connective tissue disorders, dermatographia was reported in 82% of patients (93% response rate). This oral formulation is unique because it is capable of stimulating the post-ganglionic nicotinic acetylcholine receptors, without exceeding Upper Tolerable Limits of the ingredients.

Not intending to be bound by theory, and in no way a limitation of the present invention, the invention (excluding nicotine) can be used to stimulate (and continue to maintain) organ function along the digestive tract. Because the parasympathetic nervous system mainly uses acetylcholine as its neurotransmitter and in the case of digestion and gastric emptying, acetylcholine also stimulates the release of stomach acid, cholecystokinin (which encourages secretion of pancreatic digestive enzymes), hepatic bile production, contraction of the gall bladder and the relaxation of the Sphincter of Oddi (delivering bile into the duodenum). The invention is effective in treating/preventing disorders of the gastrointestinal tract including constipation, gastroparesis, idiopathic gastrointestinal dysmotility, ileocecal valve dysfunction, ileus, low gall bladder ejection fractions, biliary dyskinesia, acalculous gall bladder disease, Sphincter of Oddi dysfunction, poor kidney function, non-alcoholic steatohepatitis (or "NASH") and non-alcoholic fatty liver disease by triggering post-ganglionic nicotinic acetylcholinergic receptors, and by stimulating the release of cholecystokinin (which must occur when acetylcholinergic agonists are effective).[45]

Not intending to be bound by theory, and in no way a limitation of the present invention, it has also been found that the formulation of the present invention is also effective in treating the neurological causes of dry eyes (assuming the lacrimal gland is not fibrotic or otherwise destroyed, or damage to or blockage of the interlobular ducts has not occurred). This method of treatment disclosed herein is unique for following reasons: (1) it is the only known non-prescription oral medication to treat the neurological cause of dry eyes; and/or (2) it can also correct dry eyes due to poor gastrointestinal absorption of the components of acetylcholine, especially crucial with genetic defects requiring the intake and absorption of higher than normal levels of some nutrients, which we have found to be common in autonomic dysfunction. Dartt D[46] teaches us that cholinergic agonists stimulate lacrimal gland protein and fluid secretion. It is well known that anticholinergic medications (such as antihistamines, atropine and others) can cause dry eyes, offering indirect evidence for cholinergic stimulation of lacrimal gland secretion. Typical of post-ganglionic parasympathetic nerves, acetylcholine release triggers the muscarinic glandular secretory response of the acinar cells of lacrimal gland. Although not obvious to those in the art, the oral administration of the invention (excluding nicotine) was effective in dramatically reducing symptoms and signs of dry eye syndrome.

The present invention can be used to increase nitric oxide formation, needed to maintain proper endothelial health and avoid thromboses (a frequent cause of aneurysms in disorders of connective tissue.)[47]. Vascular endothelial health is considered essential to avoid arterial inflammation, but also venous stenosis (chronic cerebrospinal venous stenosis, for example) which, whether intracranial or extracranial, can contribute to high intracranial pressure and symptoms thereof. An increase in availability of acetylcholine can naturally increase the availability of nitric oxide.[48] This is especially important in the conditions associated with autonomic dysfunction, as many of them are pro-thrombotic.

A dosage unit for use of the composition of the present invention may be a single compound or mixtures thereof with other compounds. The compounds may be mixed together, form ionic or even covalent bonds. The composition of the present invention may be administered in oral, intravenous (bolus or infusion), intraperitoneal, subcutaneous, transdermal, transcutaneous, intrapulmonary, intranasal, suppositories, or intramuscular form, including prenatally, all using dosage forms well known to those of ordinary skill in the pharmaceutical arts (the only exception is that use of nicotine needs to be transdermal, vaginal suppository or anal suppository). Depending on the particular location or method of delivery, different dosage forms, e.g., tablets, capsules, pills, powders, granules, liquids, elixirs, tinctures, suspensions, syrups, and emulsions may be used to provide the composition of the present invention to a patient in need of therapy for a medical condition or symptom. The composition may also be administered as any one of known salt forms. Note that nicotine should only be delivered as a transdermal, or vaginal or anal suppository.

The composition of the present invention is typically administered in a mixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the composition may be formulated to provide, e.g., maximum and/or consistent dosing for the particular form for oral, vaginal, rectal, topical, transdermal, subcutaneous, intravenous injection or parenteral administration. While the composition may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: [49]; [50]; [51]; [52]; [53]; [54]; [55]; all of which are incorporated by reference, and the like, relevant portions incorporated herein by reference.

For example, the composition may be included in a tablet or capsule. Tablets or capsules may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with an non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

The composition may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

The composition may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylaspartamidephenol, or polyethyleneoxide-polylysine substituted with palmitoyl residues, mixtures thereof, and the like. Furthermore, the composition may be coupled one or more biodegradable polymers to achieve controlled release of the composition, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In one embodiment, gelatin capsules (gelcaps) may include the composition and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

For oral administration in a liquid dosage form, the oral drug components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water soluble salt of the active ingredient, suitable stabilizing agents, and if necessary, buffering salts. Antioxidizing agents such as sodium bisulfite, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propyl-paraben, and/or chlorobutanol. Suitable pharmaceutical carriers are described in Remington's Pharmaceutical Sciences, Mack Publishing Company[56], a standard reference text in this field, relevant portions incorporated herein by reference.

For direct delivery to the nasal passages, sinuses, mouth, throat, esophagus, trachea, lungs and alveoli, the composition (excepting nicotine) may also be delivered as an intranasal form via use of a suitable intranasal vehicle. For dermal and transdermal delivery, the composition may be delivered using lotions, creams, oils, elixirs, serums, transdermal skin patches and the like, as are well known to those of ordinary skill in that art. Parenteral and intravenous forms may also include pharmaceutically acceptable salts and/or minerals and other materials to make them compatible with the type of injection or delivery system chosen, e.g., a buffered, isotonic solution. Examples of useful pharmaceutical dosage forms for administration of composition may include the following forms.

Capsules. Capsules may be prepared by filling standard two-piece hard gelatin capsules each with 10 to 500 milligrams of powdered active ingredient (e.g., a composition to be taken TID, the daily dose may comprise: about 270-1,620 mg of L-alpha glycerylphosphorylcholine; 75-450 mcg of huperzine A; 150-900 mg of Acetyl-L-Carnitine, and optionally 30-180 mg Thiamin (also known as Thiamine or Vitamin B-1).

Soft Gelatin Capsules. A mixture of active ingredient is dissolved in a digestible oil such as soybean oil, cottonseed oil or olive oil. The active ingredient is prepared and injected by using a positive displacement pump into gelatin to form soft gelatin capsules containing, e.g., 100-500 milligrams of the active ingredient. The capsules are washed and dried.

Tablets. A large number of tablets are prepared by conventional procedures so that the dosage unit was 100-500 milligrams of active ingredient, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

To provide an effervescent tablet appropriate amounts of, e.g., monosodium citrate and sodium bicarbonate, are blended together and then roller compacted, in the absence of water, to form flakes that are then crushed to give granulates. The granulates are then combined with the active ingredient, drug and/or salt thereof, conventional beading or filling agents and, optionally, sweeteners, flavors and lubricants.

Injectable solution. A parenteral composition suitable for administration by injection is prepared by stirring 1.5% by weight of active ingredient in deionized water and mixed with, e.g., up to 10% by volume propylene glycol and water. The solution is made isotonic with sodium chloride and sterilized using, e.g., ultrafiltration.

Suspension. An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

For mini-tablets, the active ingredient is compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

For rectal and vaginal routes of administration, the composition of the present invention can be formulated as solutions, retention enemas, suppositories or ointments containing conventional suppository bases such as cocoa butter or other glycerides. Suppositories may also include about 0.5% to about 50% of a compound of the invention, disposed in a polyethylene glycol (PEG) carrier, for example, PEG 1000 (96%) and PEG 4000 (4%).

An exemplary transdermal device generally includes a reservoir defined by an impermeable backing layer and a membrane. The backing layer and the membrane are joined together about the outer periphery of the device. These layers may be joined by an adhesive, a heat seal, or the like. The transdermal device may also include an adhesive layer to attach the device to the skin of a subject. A release liner will generally cover the adhesive that the user removes prior to use of the device to expose adhesive layer.

Backing layer defines the distal side of the patch, that is, the side furthest from the skin in use. The backing layer functions as the primary structural element of the device and provides the device with its mechanical properties, e.g., flexibility. The backing layer serves as a protective, impermeable covering to prevent loss of the particles containing the active compound(s) in the reservoir. Suitable backing materials include commercially available films for medical use, such as those supplied by 3M corporation, Dow Chemical or Fasson Medical Industries. Typical backing materials are made from polyester or the like and may be pigmented or metallized.

The reservoir is defined generally by the space or gap between the backing layer and the membrane, provides a storage structure in which to retain the suspension of particles containing the active compound(s) to be administered. One side of the reservoir is generally defined by a highly porous member that retains the formulation within the reservoir, i.e., it deters bulk flow of the formulation out of the reservoir, but allows passage of the formulation from the reservoir into the skin. Materials suitable for use as membrane include nonwoven fabrics such as nonwoven polyesters, polyethylene, polypropylene and other synthetic polymers. The material is heat or otherwise sealable to the backing layer to provide a barrier to transverse flow of reservoir contents.

Adhesive layer is the means by which the device is affixed to the skin. This layer is made from a pharmaceutically acceptable pressure sensitive adhesive, such as polydimethylsiloxane, polyisobutylene, polyacrylate, polyurethane and the like. It will be appreciated that the adhesive layer can also be a peripheral, or rim, adhesive layer.

The transdermal device containing the particles containing active compound(s) may also include a peel strip or release liner to cover the surface of the adhesive layer and to prevent loss of reservoir contents during storage. Prior to use, the release liner is removed from the device. The release liner is typically a material impermeable to the reservoir contents, for example polyethylene terephthalate, and is releasable usually by treatment with a silicone or fluorocarbon.

Transdermal devices generally include a backing layer, a membrane and a peripheral adhesive layer. The backing layer and membrane may be glued or heat-sealed about the periphery of the device. A reservoir defined by the space between the backing layer and the membrane provides for storage of particles containing the active compound(s) to be administered transdermally. The peripheral adhesive layer may be applied directly to backing layer. A release liner protects the device during storage.

The contents of the reservoir may even be in direct contact with the skin when the device is affixed to a subject. The reservoir in this device is composed of an absorbent sponge or a porous, highly permeable polymer. Materials suitable for the reservoir include polyurethane, polyethylene or polypropylene materials. An impermeable backing layer prevents loss of reservoir contents through the distal, top side of the device. The backing layer is coated on its distal side with an adhesive overlay, which is protected by a backing or polymer layer. Prior to use, the peripheral edge of the adhesive overlay is exposed by peeling a release liner and an impermeable protective strip from the proximal, skin side of the device. The transdermal delivery device may be adhesively attached to the skin of the user, although other methods for attaching the device to the skin are contemplated and suitable, e.g., an elastic arm band or an adjustable belt.

Transdermal device membranes are generally porous, highly permeable membranes with minimal resistance to diffusion of the reservoir contents, relative to the skin. At the same time, the membrane functions to prevent bulk flow of the particles containing the active compound(s) in the reservoir. Materials suitable for use as a membrane include hydrophilic and hydrophobic fabrics, cloths and polymer films having a porosity suitable for retaining the particles containing the active compound(s). Such materials may be non-woven or woven, yet having a defined pore size. It will be appreciated that the membrane can be selected to provide more or less diffusional resistance as desired. For example, to design a device where the membrane is rate controlling, rather than the skin, a membrane with a tighter weave or smaller pore size can be selected.

Kits. The present invention also includes pharmaceutical kits useful, for example, for the treatment of medical conditions associated with the diseases discussed hereinabove, which comprise one or more containers containing a pharmaceutical composition comprising a therapeutically effective amount of the components of the composition. Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

TABLE 1 the present invention can have the following formula and dosing regimen.

| Substance | Final dose amount | Range for Daily Dose | Range per dose taken TID | Dosage range if dose is halved, when taken TID |
|---|---|---|---|---|
| Alpha GPC (50% elemental) | 600 mg | 1,200-2,400 mg | 400-800 mg | 200-400 mg |
| Huperzine A | 150 mcg | 300-600 mcg | 100-200 mcg | 50-100 mcg |
| Acetyl L-Carnitine | 300 mg | 450-1,800 mg | 150-600 mg | 75-300 mg |
| Optional: Thiamin | N/A or 30 mg | N/A or 30-90 mg | N/A or 10-30 mg | N/A or 5-15 mg |
| Optional: Magnesium | 30 mg | 1-300 mg | 0.3-100 mg | N/A or 0.15-50 mg |

TABLE 2 the present invention can also have the following formula and dosing regimen.

| Substance | Final dose amount | Range for Daily Dose | Range per dose taken TID | Dosage range if dose is halved, when taken TID |
|---|---|---|---|---|
| Alpha GPC (50% elemental) | 270 mg | 270-1,620 mg | 90-540 mg | N/A |
| Huperzine A | 75 mcg | 75-450 mcg | 25-150 mcg | N/A |
| Acetyl L-Carnitine | 150 mg | 150-900 mg | 50-300 mg | N/A |
| Optional: Thiamin | 30 mg | 30-180 mg | 10-60 mg | N/A |
| Optional: Magnesium | 30 mg | 1-300 mg | 0.3-100 mg | N/A |

Other recipes of the present invention include:

A tablet or capsule (e.g., a vegetarian capsule) comprising: at least one of choline, lecithin, or L-Alpha Glycerylphosphorylcholine ("Alpha GPC"): 600 mg (e.g., if 50% elemental), Acetyl-L-Carnitine: 300 mg, Huperzine A: 150 mcg, and optionally 10-30 mg Thiamin and/or 0.3 to 100 mg Magnesium. In certain examples the dosage for can be halved and provided in a dosage of two capsules per dosage, taken 1-3 times per day.

Nicotine, e.g., 3 to 21 mg nicotine patch can be used alone, for short periods of time (if the patients do not exhibit skin irritation, skin welting and/or dermatographia) to test the viability of the post-ganglionic nicotinic acetylcholinergic receptors and/or effector organs, or for short-term treatment, especially useful in ileocecal valve dysfunction and gastroparesis The composition may also include: a choline compound selected from at least one of choline at 100 mg to 1,000 mg, lecithin at 100 mg to 3 grams, or L-alpha glycerylphosphorylcholine at 30 mg to 2,400 mg; 100-200 mcg of huperzine A; 150-600 mg of Acetyl-L-Carnitine and optionally 10-30 mg Thiamin and/or 0.3 to 100 mg Magnesium.

A dose, e.g., a tablet, capsule or liquid, that includes a choline compound selected from at least one of choline at 100 mg to 1,000 mg, lecithin at 100 mg to 3 grams, or L-alpha glycerylphosphorylcholine at 30 mg to 2,400 mg; 150 mcg of huperzine A; 300 mg of -Acetyl-L-Carnitine, and optionally Thiamin and Magnesium as needed.

A composition reflecting the complete daily dosage consisting essentially of: a choline compound selected from at least one of choline at 100 mg to 1,000 mg, lecithin at 100 mg to 3 grams, or L-alpha glycerylphosphorylcholine at 30 mg to 2,400 mg; 100-200 mcg of huperzine A; 150-600 mg of Acetyl-L-Carnitine, and optionally 10-30 mg Thiamin and/or Magnesium in a suitable non-active excipient.

A composition reflecting the complete daily dosage consisting of: a choline compound selected from at least one of choline at 100 mg to 1,000 mg, lecithin at 100 mg to 3 grams, or L-alpha glycerylphosphorylcholine at 30 mg to 2,400 mg; 100-200 mcg of huperzine A; 150-600 mg of Acetyl-L-Carnitine, and optionally 10-30 mg Thiamin and/or Magnesium in a suitable delivery dose.

Discussion of Ingredients:

Choline compounds may include choline, lecithin or Alpha Glycerylphosphorylcholine (also known as "Alpha-GPC" or "choline alfoscerate"), which is a natural choline compound and is a parasympathomimetic acetylcholine precursor[20]. Alpha-GPC is derived from highly purified soy lecithin and is a biosynthetic precursor of the acetylcholine neurotransmitter (contributing the "choline" component)[21]. Current research indicates that the recommended "Adequate Intake" for choline is not sufficient in numerous patients, including postmenopausal women and those with common genetic polymorphisms[57][58]. Additionally, because many patients with chronic diseases attempt to lower inflammation by eliminating meat and eggs from their diet, they may be avoiding the main sources for dietary choline. Most importantly, however, this composition was designed to incorporate ingredients in sufficient quantities to stimulate the post-ganglionic nicotinic acetylcholinergic receptors in order to successfully stimulate the target organs to function, regardless of the patient's dietary requirements or genetic polymorphisms. The quantities must be taken in the amounts designated in order to be sufficient to trigger post-ganglionic nicotinic acetylcholinergic response (much as a sudden burst of transdermal nicotine will accomplish). If the same ingredient amounts are taken in small quantities throughout the day, the post-ganglionic nerve will not be triggered to respond. This is why the composition of the dosing is critical for this invention.

Genetic defects resulting in the need for higher levels of choline consumption than required for the normal population were also frequently found in this patient population.

Not intending to be bound by theory, and in no way a limitation of the present invention, Acetyl-L-Carnitine supplementation is known to be beneficial in patients with chronic fatigue (a co-morbid presentation of most, if not all "autoimmune" disorders). These patients have been shown to have low levels of Acetyl-L-Carnitine in their serum.[24,25] Although likely multi-factorial, in the case studies performed, patients with organ malfunction secondary to poor vagus nerve function invariably achieved better organ function when Acetyl-L-Carnitine was added to the compound. Another reason for its success may be because it acts as a precursor of acetylcholine, through the use of Carnitine acetyltransferase, rather than Choline acetyltransferase. For patients who are unable (for numerous potential reasons) to produce enough Choline acetyltransferase to allow contribution of the acetyl group of acetyl Co-A to produce substantial acetylcholine, Acetyl-L-Carnitine provides another method for donation of the acetyl group, and the use of a different enzyme to do so (Carnitine acetyltransferase, rather than Choline acetyltransferase).[27] Thus, genetic abnormalities in the production of choline acetyltransferase can contribute to the need for supplementation with Acetyl-L-Carnitine, and were indeed, found to be common in this patient population.

Huperzine A is a compound found in the plant *Huperzia serrata* and is a potent acetylcholinesterase inhibitor. Its action thus increases acetylcholine levels in the brain and periphery by slowing the destruction of acetylcholine in the synapse[28]. Cholinesterase inhibitors may also decrease norepinephrine levels, which, by definition, are typically abnormally high in the hyperadrenergic postural orthostatic tachycardia" patient ("Hyperadrenergic POTS"), making this a unique composition for successful treatment for patients with hyperadrenergic POTS (one of the forms of autonomic dysfunction in this patient population).[29, 30, 31]

Nicotine is a powerful nicotinic agonist found in the leaves of the tobacco plant (*Nicotiana tabacum*). Transdermal nicotine (3-21 mg) stimulates post-ganglionic nicotinic receptors, thus enhancing parasympathetic neurotransmission. Its dose is critical because at higher concentrations, it possesses some antagonist effects at the nicotinic receptors. This higher dose can stimulate the heart eliciting the Bezold-Jarisch reflex (bradycardia, hypotension, nausea) and may eventually result in weakness, tremors, and convulsions. A dosage of 60 mg is lethal.[32] In patients tested, transdermal nicotine (3-21 mg) never failed to open the ileocecal valve in the patients with poor vagus nerve function, whenever the ileocecal valve was not physically damaged. Oral doses of nicotine were ineffective at opening the ileocecal valve, or at arresting gastroparesis/chronic constipation.

Nicotine can be used as a diagnostic tool or short-term treatment to stimulate the post-ganglionic nicotinic acetylcholine receptors and can result in correction of: constipation, gastroparesis, idiopathic gastrointestinal dysmotility, ileocecal valve dysfunction ("ileus").

Thiamin (also known as Thiamine or Vitamin B-1) deficiency (which can wax and wane in these conditions) is commonly seen in this patient group as a tardive consequence of disrupted bowel and organ function. Thiamin levels can also drop due to a diet low in thiamin, chronic diarrhea, anorexia, alcoholism and in patients taking medications including, but not limited to diuretics, quercetin and rutin, and/or in patients low in transketolase. It is important to note that the FDA has not established a tolerable upper intake level of Vitamin B-1. Thiamin may be provided in any of the following forms: Allithiamine, aneurine, aneurine HCl, aneurine mononitrate, antiberiberi factor, antiberiberi vitamin, antineuritic factor, antineuritic vitamin, anurine, B-complex vitamin, benfotiamine, beta-hydroxy-ethylthiazolium chloride, sulfotiamine, thiamin, thiamin chloride, thiamin diphosphate, thiamin HCl, thiamin hydrochloride, thiamin monophosphate (TMP), thiamin nitrate, thiamin pyrophosphate (TPP), thiamin triphosphate (TTP), thiamine, thiamine chloride, thiamine diphosphate, thiamine HCl, thiamine hydrochloride, thiamine monophosphate (TMP), thiamine nitrate, thiamine pyrophosphate (TPP), thiamine tetrahydrofurfuryl disulfide, thiamine triphosphate (TTP), thiaminium chloride HCl or thiaminium chloride hydrochloride.

Thiamin deficiency can cause neurological and cardiovascular consequences ("Wernicke-Korsakoff syndrome). What is unique in this patent is the surprising finding that its inclusion is necessary for patients suffering with autonomic dysfunction, as is seen in patients with genetic and/or acquired disorders of collagen (which may include Ehlers-Danlos syndrome, Marfan's syndrome, Loeys-Dietz syndrome, Stickler syndrome, fibrillary disorders, elastin disorders, Joint Hypermobility Syndrome), chronic infectious and/or fatigue syndromes (which may include Chronic Fatigue Syndrome, Myalgic Encephalomylitis, Chronic Lyme disease, fibromyalgia), autoimmune disorders (which may include multiple sclerosis), mental trauma, a vascular disease and a rheumatological disease. These patients report gastrointestinal disturbances that may wax and wane to some degree, but continue to manifest over months, years and even lifetimes. These gastrointestinal disturbances, including chronic constipation, gastroparesis (often punctuated with severe diarrhea), low gall bladder ejection fractions, biliary dyskinesia, acalculous gall bladder disease, Sphincter of Oddi dysfunction, non-alcoholic steatohepatitis, non-alcoholic fatty liver disease, ileocecal valve dysfunction, and dysmotility can ultimately result in gastrointestinal inflammation, diverticulitis, mast cell activation, multiple food allergies and poor nutrient absorption (including poor absorption of Thiamin). Patients exhibit signs and symptoms of the numerous neurological and cardiovascular consequences of Thiamin deficiency, but because these symptoms come and go, they do not fit the strict criteria for diagnosis of Wernicke-Korsakoff syndrome (including beriberi). This composition reverses symptoms of delusions, difficulty walking, numbness and nystagmus, but supplementation with oral Thiamin alone will not eliminate disease. The compound must also include a choline compound, an anticholinesterase compound and Acetyl-L-Carnitine to stimulate organ function to allow absorption of oral thiamin. Magnesium can be added to assist in Thiamin absorption.

Not intending to be bound by theory, and in no way a limitation of the present invention, many of these patients suffer with additional disorders which can exacerbate potentially low levels of Thiamin. Co-morbid disorders, although not essential to the disease condition, cause a more rapid and aggressive decline in patient health. Patients with Crohn's disease, Celiac Disease and those who have had surgery for bariatric conditions ("lap-band" surgery and sleeve gastrectomies[59] can suffer from a more aggressive decline. Such conditions result in poor breakdown of ingested food and/or poor absorption of nutrients such as magnesium and folic acid (which deplete the body's stores of Thiamin).

Other co-morbid conditions involve the consumption of Thiamin antagonists. Such antagonists include sulfites (a preservative), raw fish and shellfish, bacterial thiaminases, and quercetin and rutin (common supplements ingested in this patient population). The subject patient population commonly suffers from conditions including intracranial hypertension, pseudotumor cerebri, edema, lymphedema, pitting edema, pulmonary fluid retention and other disorders of lymph fluid and cerebrospinal fluid regulation, requiring chronic use of acetazolamide, furosemide and other diuretics.[60] Diuretics, sugar, coffee, tannins found in tea, nicotine and alcohol use contributes to the body's loss of Thiamin.

Human storage of Thiamin is believed to be 25 to 30 mg, but once this store is depleted, many patients appear to be on the borderline of complete Thiamin deficiency. After patients have been ill for months to years, any dip in systemic Thiamin levels becomes immediately evident. For example, the ingestion of even small amounts of ethanol often results in nystagmus in many of these patients. This inability to metabolize even small amounts of alcohol occurs because Thiamin plays a key metabolic role in the cellular production of energy, mainly through glucose metabolism. Thiamin is required to metabolize ethanol, converting it to carbon dioxide and water. Thiamin administration in a patient who has untreated poor vagus nerve function will not be effective, unless Thiamin is administered after repeated stimulation of the vagus nerve via the patented compound, or via the injection of Thiamin, which can bypass the gastrointestinal tract. Thiamin deficiency is also suggested by almost universal reports of hypothermia in conjunction with weight loss for no apparent (or medical) reason. Because Thiamin helps convert carbohydrates to fat for storage and potential energy, many patients lose about 20% of their body weight, and many are accused of having eating disorders. The combination of poor nutrient absorption with the discomfort and frank pain associated with gastroparesis often results in dramatic weight loss and food avoidance behavior. Such depletion can wax and wane based on numerous factors, including but not limited to: patient position and activity level (some positions of the body exacerbate or relieve some vagus nerve compression), blood volume, diet, infection and the intake of thiaminases.

Thiamin (also known as Thiamine or Vitamin B1) can be found in a variety of foods, and is in relatively high concentration in foods often avoided by patients prone to gastrointestinal disruption, including white flour, gluten, and whole wheat. In our studies, we found that patients with autonomic dysfunction as seen in patients with genetic and/or acquired disorders of collagen (which may include Ehlers-Danlos syndrome, Marfan's syndrome, Loeys-Dietz syndrome, Stickler syndrome, fibrillary disorders, elastin disorders, Joint Hypermobility Syndrome), chronic infectious and/or fatigue syndromes (which may include Chronic Fatigue Syndrome, Myalgic Encephalomylitis, Chronic Lyme disease, fibromyalgia), autoimmune disorders (which may include multiple sclerosis), mental and/or physical trauma, a vascular disease and a rheumatological disease, often suffered with chronic candida infections of the esophagus, tongue ("thrush") and vagina. In a survey of 192 patients with autonomic dysfunction and/or connective tissue disorders, chronic candida infection was reported in 70% of patients (81% response rate). Thus, these patients often avoided another good source of Thiamin—Brewer's yeast, yeast and peanuts (commonly known to be high in yeast). This formulation will not only replenish low Thiamin levels, it is also needed to restore normal gastric acid secretion, eliminating the alkaline environment in which candida (and other fungi) thrive.

Oral magnesium supplementation may be in one or more of the various forms available, including but not limited to: Magnesium chloride, oxide, gluconate, malate, orotate, glycinate, L-threonate and citrate. The addition of magnesium and the avoidance of magnesium deficiency is important not only to eliminate symptoms of magnesium deficiency, but when magnesium deficiency is present, proper patient response to thiamin is diminished.[61] Thus, in this composition, when thiamin is added, it is accompanied by the addition of magnesium.

Not intending to be bound by theory, and in no way a limitation of the present invention, the invention can be used as an addition to a normally prescribed pre-natal vitamin in order to prevent vascular abnormalities, such as inadequate veins and chronic cerebrospinal venous insufficiency (which can also result in any form of increased intracranial hypertension), through moderation of angiogenesis in the fetal brain and in vessels draining the brain. Such moderation of angiogenesis has proven to be critical in the development of the hypothalamus.[62] Studies show that patients with connective tissue disorders and vascular disorders exhibit abnormal amygdala, which can affect memory from childhood, and continue throughout the patient's life. This results in a decline in spatial relationship and proprioceptive representations.[63,64] Previous studies in rats showed that maternal dietary choline supplementation increases the size of the cell body of cholinergic neurons and decreases choline acetyltransferase activity in brain, whereas choline deficiency decreases cholinergic activity in the offspring's brain. The embryologic timing of neurogenesis results in deficiencies in spatial learning, long-term memory and temporal processing. Because these abnormalities are permanent, prevention of such vascular and neurological abnormalities must be avoided via treatment of the mother throughout her pregnancy. The addition of choline is not sufficient when the mother has poor gastrointestinal absorption of nutrients (as is seen in autonomic dysfunction, for example). The compound including a choline compound, an anticholinesterase compound and Acetyl-L-Carnitine is needed to stimulate proper organ function (and therefore normal nutrient absorption) via stimulation of the post-ganglionic acetylcholine receptor. Thus, for use with the present invention, the addition of Thiamin/Magnesium are optional in the composition.

Thus, although patients initially report autonomic dysfunction (including dysfunction of the organs controlled by the vagus nerve), such organ dysfunction (often in conjunction with genetic defects involving the production or release of acetylcholine and the exposure to thiaminases) eventually leads to Thiamin deficiency, contributing to poor acetylcholine production needed for the lacrimal gland's production of the aqueous layer of tears and the salivary gland's production of saliva, ultimately resulting in dry eyes and/or dry mouth, waxing and waning to some degree.

The composition and method of use of the present invention is also unique because it corrects for these numerous causes of dysfunction and includes ingredients in the quantities and form required to work around the genetic, vascular, and/or co-morbid components involved. IBS/gastroparesis/constipation was initially targeted. In patient studies, a response to medication (a bowel movement) occurred within 2-12 hours, without exception. Patients were identified with a mix of co-morbid conditions including chronic fatigue syndrome, fibromyalgia, joint hypermobility and autonomic dysfunction.

Figure 1B:
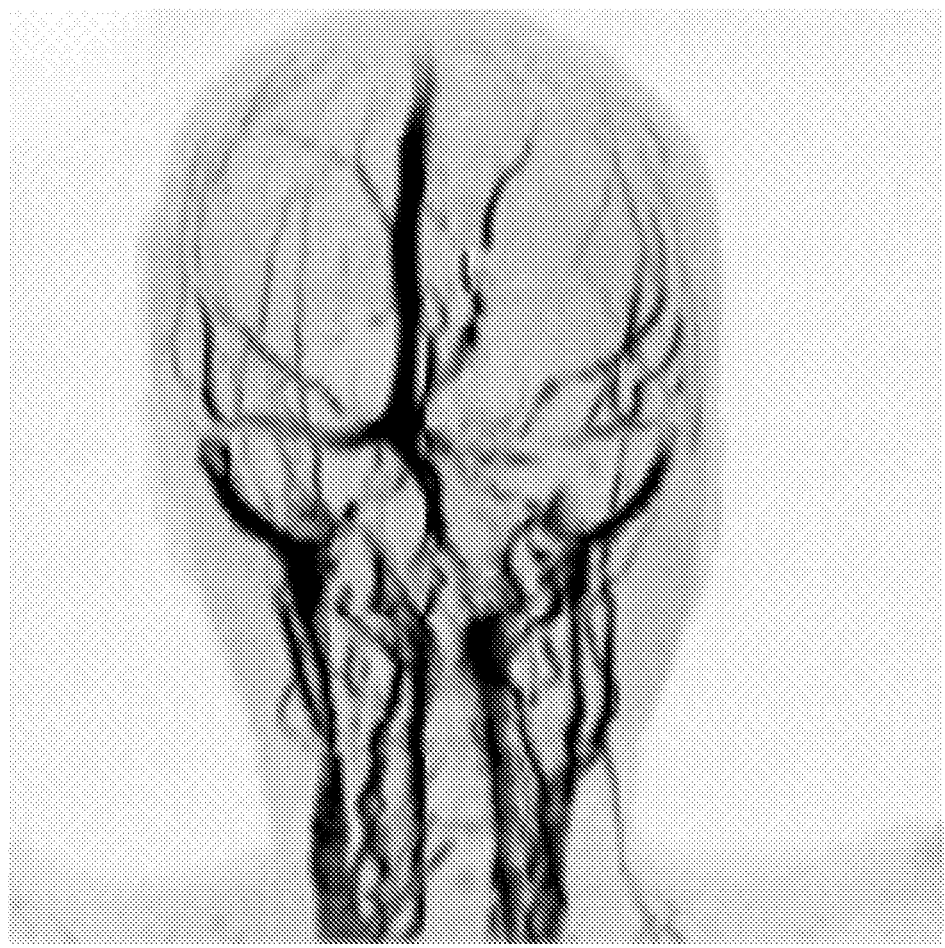
Figure 1C:
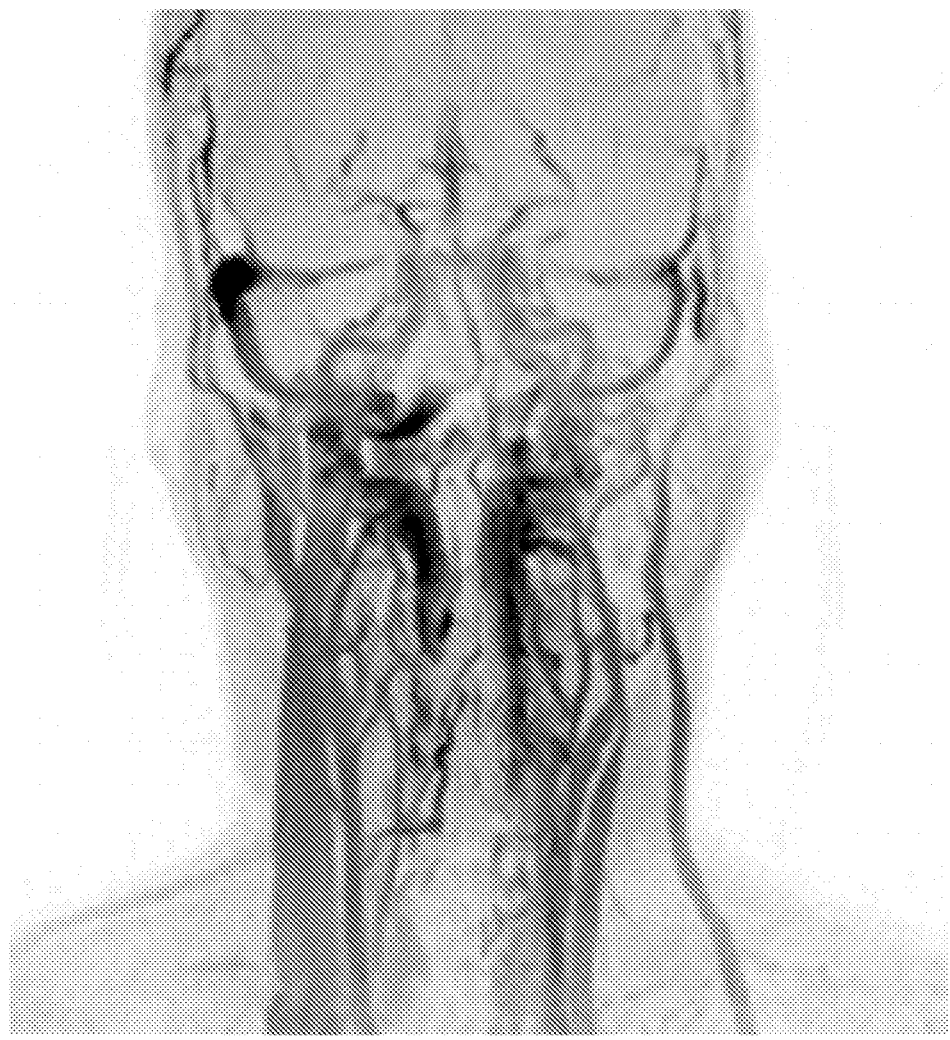

FIGS. 1A to 1C shows examples of enlargement of internal jugular veins in patients with Joint Hypermobility, Autonomic Dysfunction. FIG. 1A is an fMRI of 15 year old male: Note the abnormally large internal jugular vein (red arrow). FIG. 1B is an fMRI of 35 year old female: Note enlargement of internal jugular vein ("IJV") (red arrow). FIG. 1C is an fMRI of a 55 year old female: Note the grossly enlarged internal jugular vein (red arrow)

Figure 2A:
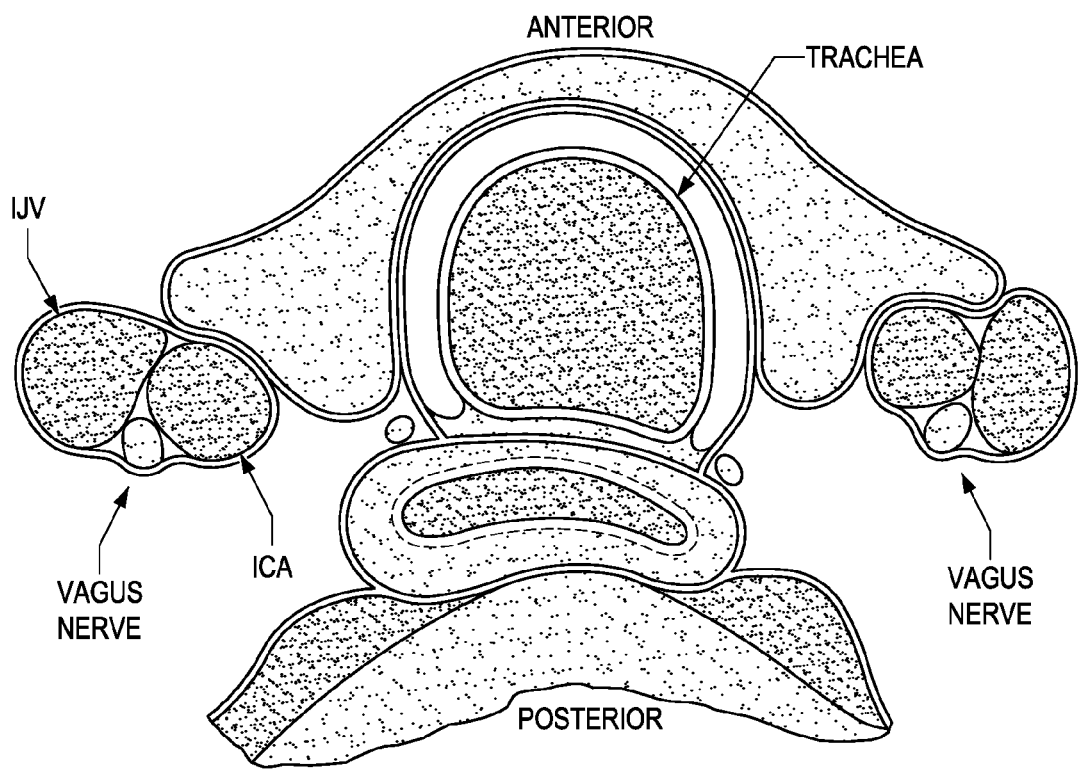
FIGS. 2A and 2B are a drawing of Structures inside Carotid Sheath (2A) and Patient image of enlarged IJV (2B a side and a cross-sectional view).
Figure 2B:
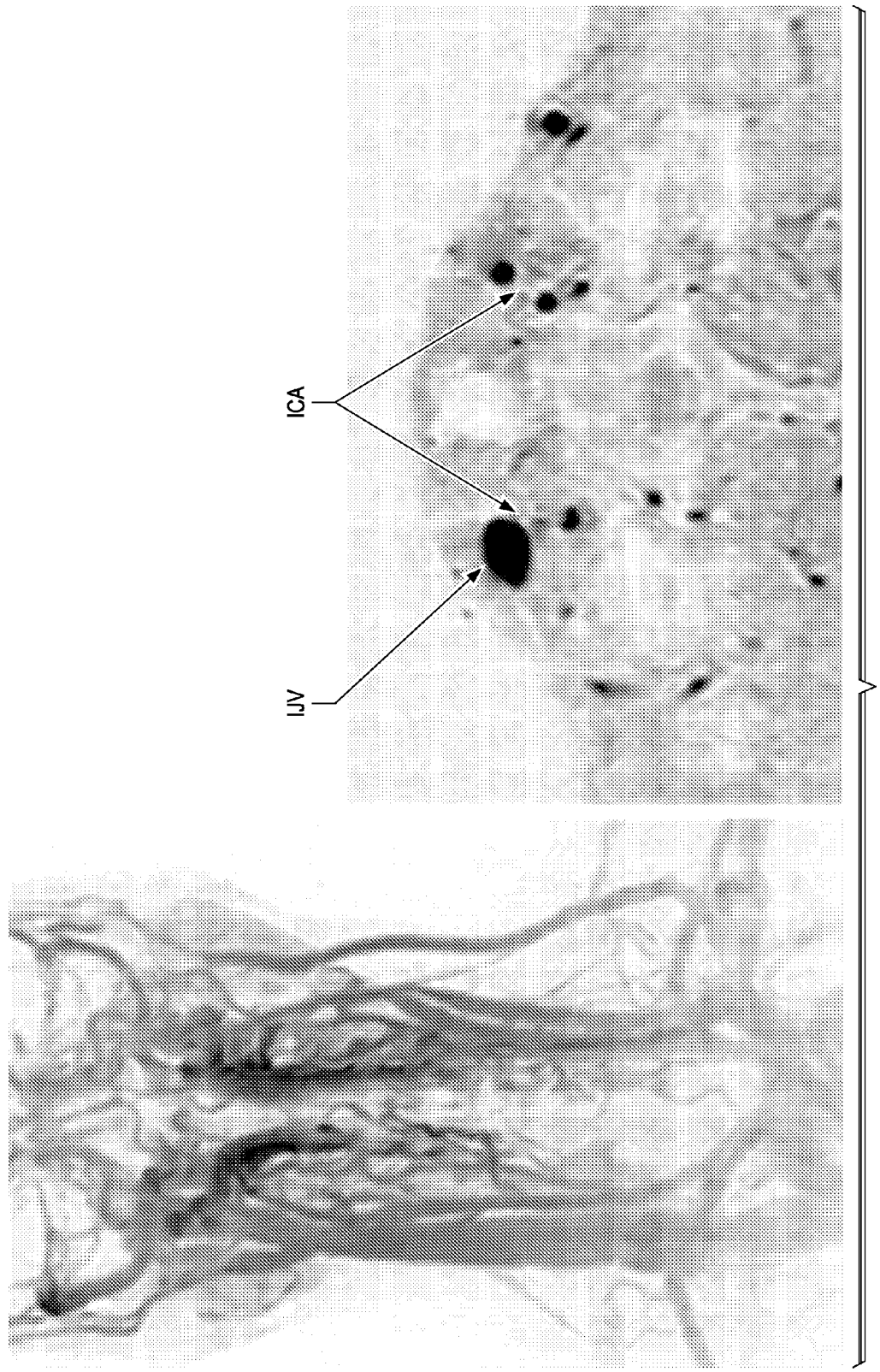

FIG. 2A shows drawing of structures inside Carotid Sheath and FIG. 2B shows a side view and a cross-sectional view of a patient image showing an enlarged IJV.

Study Results.

Results of symptoms surveys from 180 patients with connective tissue disorders and/or autonomic dysfunction (often seen in chronic fatigue syndromes): (percent positive for each symptom when the patient did not answer "I don't know"):

32% Abnormal liver enzymes indicating non-alcoholic steatohepatitis or "NASH" or non-alcoholic fatty liver disease, (with a 48% response rate).

34% Low gall bladder ejection fractions (biliary dyskinesia, acalculous gall bladder disease) (with a 35% response rate).

86% Constipation, gastroparesis, idiopathic gastrointestinal dysmotility, and/or ileocecal valve dysfunction (with a 98% response rate).

37% Low pancreatic enzymes (with a 9.9% response rate).

75% Dry eyes (with a 93% response rate).

76% Dry mouth (xerostomia) (with a 94% response rate).

70% Chronic candida infections (with a 81% response rate).

The present composition was provided to a number of patients having certain diagnosed diseases, as summarized in Table 1 above and suffering from a variety of medical conditions or symptoms associated with those diseases, again, as summarized above. The following case studies demonstrate the effectiveness of the composition and methods of the present invention.

Patient 1: 55 year old female; Diagnoses: joint hypermobility (judged by the Beighton Scale), autonomic dysfunction (patient failed the Tilt Table Test of autonomic function) and visual and auditory hallucinations, hypothermia. Patient was diagnosed with hyperadrenergic POTS ('hyperadrenergic postural orthostatic tachycardia syndrome') when blood levels of norepinephrine (after standing for 10 minutes) were found to be high (normal readings are 0-600 pg/ml. Patient's readings were over 750 pg/ml). Patient tried numerous medications, including Physostigmine, but was unresponsive. Patient developed chronic candida infections—esophageal, gastrointestinal and vaginal. Patient was found to have an abnormally enlarged internal jugular vein on her right side, potentially compressing her vagus nerve intermittently. Disease progression: Patient had motion sickness throughout her life, but after developing a virus at the age of 46, she developed high intracranial pressure, gastroparesis, constipation, ileocecal valve dysfunction (confirmed by urologist with barium imaging), IBS-like symptoms, tachycardia, hyperadrenergic "POTS", dry eyes (TBUT) ("tear break-up time") of zero and no measurement of tear production via Schirmer strips over 10 minutes), low gall bladder ejection fractions, abnormal liver enzymes, abnormal kidney function (which would wax and wane) and visual and auditory hallucinations over an eight year period. This patient's mother also has at least one defect of choline metabolism. Carbonic anhydrase inhibitors relieved symptoms of high intracranial pressure, and ingestion of the compound three times per day resulted in complete resolution of her remaining symptoms. (A trial with 7 g of transdermal nicotine near the ileocecal valve opened the valve overnight. It also induced intractable itching, redness, and skin welting at which time she switched to the oral compound.) After symptom resolution, the patient was able to maintain normal bowel movements by taking the compound once a day, and she continued to do so for months. Her liver enzymes and kidney function began to show abnormal readings, and pain at the site of the ileocecal valve began to occur. The patient increased ingestion of the compound to three times per day, resulting in resolution of symptoms. (Compound: Alpha GPC 300 mg, Acetyl-L-Carnitine 300 mg, Huperzine A 125 mg) Patient then added magnesium (30 mg) and thiamin (30 mg) and hallucinations resolved. Patient has continued to take the medication three times a day (TID)—(higher concentrations would sometimes result in agitation or insomnia). Patient reported resolution of hallucinations, intermittent nystagmus, dry eyes, resolution of low gall bladder ejection fraction, and a drastic decline in the frequency of esophageal candida episodes. Kidney function and liver function returned to normal levels. Tremor resolved and orthostatic intolerance improved dramatically. Norepinephrine levels (when standing) returned to normal. Resolution of livido reticularis occurred. Patient lowered her dose to once a day, and although constipation/gastroparesis was not severe, pain began to return near the site of her ileocecal valve. Patient returned to (bis in die) BID or (ter in die) TID dosing and resolution of ileocecal pain was eliminated. Improvements have continued by taking medication for a year without loss of effectiveness. Patient's IGF-1 was low/normal prior to beginning the compound. She was placed on 2 units/day of growth hormone in attempt to raise her IGF-1 levels to the upper normal range (which it did). Approximately 6 months after beginning the compound, the patient's IGF-1 levels were found to be above normal. She discontinued exogenous growth hormone therapy. Three months later, her IGF-1 levels remained at the upper end of normal ranges.

Patient 2: 14 year old male: Diagnoses: Joint hypermobility and disabling autonomic dysfunction and orthostatic hypotension, stenosed transverse sinus, and idiopathic intracranial hypertension. He tried numerous medications, including Huperzine A (prescribed for mental fatigue), with no response. He developed a virus at the age of 8, triggering his symptoms. He experienced constipation, punctuated by violent episodes of diarrhea since the age of eight. He developed symptoms of intracranial hypertension (headache at the base of the skull, nausea, sensitivity to light and sound and ringing of his ears (resolved with a carbonic anhydrase inhibitor). A retrospective analysis of his head circumferences (as compared to weight and length) demonstrated macrocephaly by the age of 15 months. A carbonic anhydrase inhibitor eliminated symptoms of high intracranial pressure. He was found to have a stenosed transverse sinus. He was unable to attend school for three years due to complete exhaustion, inability to concentrate and orthostatic intolerance. He developed extremely dry eyes with a tear break up time of zero and no tear production was measurable in 10 minutes using the Schirmer test for tear production. He developed an abnormal blink (rolling his eyes back and forcefully closing his eyes many times) due to extremely low tear production. He was found to have an abnormally enlarged internal jugular vein on his right side, potentially compressing his vagus nerve intermittently. Response to medication (compound: Alpha GPC: 275 mg, Acetyl-L-Carnitine: 300 mg, Huperzine A 125 mg—taken BID): Immediate resolution of constipation/diarrhea/"IBS-like" episodes. Dry eyes returned to normal, and his blink also returned to normal. Resolution of livido reticularis occurred. Patient takes medication two times a day (BID) and has had no resurgence of GI (gastrointestinal) symptoms, his orthostatic tolerance is almost normal, and he is able to concentrate on school-work again. Patient has continued the taking the medication for 8 months without loss of effectiveness.

Patient 3: 40 year old female diagnosed with Ehlers-Danlos syndrome, hypermobility type. Her symptoms include constipation, gastroparesis, hypothermia, dry eyes, dry mouth and visual snow, type one. She also experienced a "visual blob" in her vision (a "form constant" that eye doctors were unable to view and were uncertain as to its origin). She has been taking opioid pain-killers almost daily for 20 years. Because opioids are known to cause constipation and are often used in patients with hypermobility, she was an excellent test subject to see if the compound could over-ride the constipating effects of opioids. (Compound taken: Alpha GPC: 300 mg, Acetyl-L-Carnitine: 150 mg, Huperzine A: 125 mg, Thiamin: 20 mg, Magnesium: 30 mg—taken BID). Typical of other study patients, she responded to the compound within three hours with a normal bowel movement. Normal bowel function continued with use of the compound despite her concomitant opioid use. Her "visual blob" (form constant) disappeared within three days of use of the compound. Her visual snow remained, but because the patient also suffered with symptoms of idiopathic intracranial hypertension (and pseudo-tumor cerebri without papilledema), a retrial of the compound will be conducted after she lowers her intracranial pressure with a carbonic anhydrase inhibitor.

Patient 4: 15 year old female with joint hypermobility, headache at the base of her skull (since early childhood) and a tentative diagnosis of Classical Ehlers-Danlos syndrome and orthostatic intolerance ("POTS"), suffered with the following symptoms: IBS-like symptoms from birth, constipation, memory problems, orthostatic hypotension. She was treated with a carbonic anhydrase inhibitor, which eliminated her life-time headache, suggesting idiopathic intracranial hypertension, which in turn suggests potentially defective cranial venous outflow. (Compound taken: Alpha GPC: 270 mg, Acetyl-L-Carnitine: 150 mg, Huperzine A: 75 mg, Thiamin: 30 mg—taken TID). Use of the compound resulted in a return of normal bowel movements. Patient continues to exhibit normal kidney, liver, gall bladder and pancreas function. Orthostatic hypotension improved with the compound, and was completely eliminated after taking a histamine-blocker (H-1 antagonist), for one week (suggesting the beginnings of mast cell involvement).

Patient 5: 42 year old female with self-diagnosed hypermobility reported symptoms of constipation, gastroparesis, dry eyes and visual snow (types 1 and 2). Later, she experienced episodes of heart irregularities and exhaustion. (Compound taken: Alpha GPC: 270 mg, Acetyl-L-Carnitine: 150 mg, Huperzine A: 75 mg, Thiamin: 30 mg—taken BID). Response to the compound included normal bowel movements, resolution of heart irregularities, and resolution of exhaustion within two hours of taking the supplement. Dry eyes began to resolve within two days.

Patient 6: 48 year old male diagnosed with multiple sclerosis and CCSVI (Chronic Cerebrospinal Venous Insufficiency). His symptoms included: orthostatic hypotension, constipation, dry eyes, dry mouth, exhaustion, mental confusion, low gall bladder ejection fraction, visual snow (type 1), and seeing form constants ("worms, parasites in his vision"). (Compound taken: Alpha GPC: 270 mg, Acetyl-L-Carnitine: 150 mg, Huperzine A: 75 mg, Thiamin: 30 mg, Magnesium: 30 mg—taken TID). Response to the medication was relief of gastrointestinal symptoms within three hours. Relief of remaining symptoms occurred over two weeks. Complete resolution of visual snow was not obtained, and patient (exhibiting signs and symptoms of increased intracranial pressure and pseudo-tumor cerebri without papilledema) will begin treatment with acetazolamide to see if complete resolution of visual snow will occur with the use of the compound after the reduction of high intracranial pressure.

Patient 7: 12 year old female with joint hypermobility, as measured through the Beighton Scale has the following symptoms: difficulty breathing, seeing spiders and other form constants, tachycardia, constipation, gastroparesis, hypothermia, exhaustion, in addition to symptoms of intracranial hypertension (which were eliminated with the use of a carbonic anhydrase inhibitor). (Compound taken: Alpha GPC: 300 mg, Acetyl-L-Carnitine: 300 mg, Huperzine A: 125 mg, Thiamin: 30 mg, Magnesium: 20 mg—taken BID). Within two hours of ingesting the compound, her gastrointestinal symptoms had improved and she had normal bowel movements. Difficulty breathing stopped after 3 days on the compound, as did her exhaustion. Seeing form constants completely disappeared after one week. Her improvement in symptoms continues with TID dosing of the compound.

Patient 8: 40 year old male suffered from exhaustion, idiopathic intracranial hypertension, painfully dry eyes, dry mouth, seeing dancing lines and spiders (form constants), heart rate irregularities (large swings between bradycardia and tachycardia), POTS, constipation and gastroparesis, and visual snow (type 2). Symptoms of idiopathic intracranial hypertension were resolved with the use of a carbonic anhydrase inhibitor. (Compound taken: Alpha GPC: 270 mg, Acetyl-L-Carnitine: 150 mg, Huperzine A: 125 mg, Thiamin: 30 mg, Magnesium: 30 mg—taken TID). Constipation/gastroparesis resolved within hours of taking the compound. Dry eyes, dry mouth were eliminated within three days. The remaining symptoms subsided, although the patient still experiences episodes of visual snow (type 2), and some positional bradycardia/tachycardia.

Patient 9: 45 year old female with joint hypermobility (as measured by the Beighton Scale) became sick after a car collision, resulting in lingering and disabling symptoms of: increased intracranial hypertension (relieved with the use of a carbonic anhydrase inhibitor), breathing difficulties, tachycardia, hypothermia, constipation, gastroparesis, chronic candida infections of her tongue, esophagus, GI tract and vagina, and dry eyes. The patient's fundi showed abnormally narrowed arterioles. (Compound taken: Alpha GPC: 270 mg, Acetyl-L-Carnitine: 150 mg, Huperzine A: 75 mg—taken TID). Symptoms not due to high intracranial pressure were resolved within two days of using the compound. The only breathing difficulties she has now are due to nasal congestion and severe allergies. Candida infections are rare, yet not completely eliminated (patient also suffers with low NK cells, T cells and B cells).

Patient 10: 17 year old female with joint hypermobility (as measured by the Beighton Scale) also became ill after a rear-end vehicle collision. Her symptoms included those of increased intracranial hypertension (relieved with the use of a carbonic anhydrase inhibitor), breathing difficulties, orthostatic intolerance, gastroparesis and constipation. (Compound taken: Alpha GPC: 270 mg, Acetyl-L-Carnitine: 150 mg, Huperzine A: 75 mg—taken BID). Use of the compound has resolved her symptoms of difficulty breathing, gastroparesis and chronic constipation. Her orthostatic intolerance has markedly improved.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Abell T L, Bernstein V K, Cutts T, Farrugia G, Forster J, Hasler W L, McCallum R W, Olden K W, Parkman H P, Parrish C R, Pasricha P J, Prather C M, Soffer E E, Twillman R, Vinik A I. Treatment of gastroparesis: a multidisciplinary clinical review. Neurogastroenterol Motil 2006, 18(4):263-283.
2. Robertson D, et al. editors, Primer on the Autonomic Nervous System, second edition (New York: Academic Press) 2004, pp 1-386.

3. Siegel G. J., Agranoff B. W., Fisher S. K., Albers R. W., and Uhler M. D. (1999). "Basic Neurochemistry: Molecular, Cellular and Medical Aspects". GABA Receptor Physiology and Pharmacology. American Society for Neurochemistry. Retrieved 2008 Oct. 1.
4. Itier V, Bertrand D (August 2001). "Neuronal nicotinic receptors: from protein structure to function". FEBS Letters 504 (3): 118-25. doi:10.1016/S0014-5793(01)02702-8. PMID 11532443.
5. Levy M N, Schwartz P J, eds. Vagal Control of the Heart: Experimental Basis and Clinical Implications. Armonk, N.Y.: Futura; 1994.
6. Malik M. Heart Rate Variability; Standards of measurement, physiological interpretation, and clinical use. Circulation. 1996; 93:1043-1065.
7. Monge-Argiles J A, Palacios-Ortega F, Vila-Sobrino J A, Matias-Guiu J. Heart rate variability in multiple sclerosis during a stable phase. Acta Neurol Scand. 1998 February; 97(2):86-92. PMID: 9517857.
8. Tombul T, Anlar O, Tuncer M, Huseyinoglu N, Eryonucu B. Impaired heart rate variability as a marker of cardiovascular autonomic dysfunction in multiple sclerosis. Acta Neurol Belg. 2011 June; 111(2):116-20. PMID: 21748930.
9. Rensburg D, Ker J, Grant C, Fletcher L. Autonomic impairment in rheumatoid arthritis. International Journal of Rheumatic Diseases. August 2012; 15(4):419-26.
10. Lagana B, Tubani L, Maffeo N, Vella C, Makk E, Baratta L, Bonomo L. Heart rate variability and cardiac autonomic function in systemic lupus erythematosus. Lupus. 1996 February; 5(1):49-55. PMID: 8646226.
11. Uslu N, Akyol A, Gorgulu S, Eren M, Ocakli B, Celik S, Yildirim A, Aksu H, Nurkalem Z. Heart rate variability in patients with systemic sarcoidosis Ann Noninvasive Electrocardiol. 2006 January; 11(1):38-42. PMID: 16472281.
12. Bernardi L, Passino C, Porta C, Anesi E, Palladini G, Merlini G. Widespread cardiovascular autonomic dysfunction in primary amyloidosis: does spontaneous hyperventilation have a compensatory role against postural hypotension? Hear. 2002 December; 88(6):615-621.
13. Fin Z J, Lester S, Lu T, Keen H, Boundy K, Proudman S, Tonkin A, Rischmueller M. Mild autonomic dysfunction in primary Sjogren's syndrome: a controlled study. Arthritis Research & Therapy 2008, 10:R31.
14. Beaumont A, Burton A, Lemon J, Bennett B, Lloyd A, Vollmer-Conna U. Reduced Cardiac Vagal Modulation Impacts on Cognitive Performance in Chronic Fatigue Syndrome. November 2012. PloS ONE 7(11):e9518.
15. Bohora S. Joint hypermobility syndrome and dysautonomia: expanding spectrum of disease presentation and manifestation. Indian Pacing Electrophysiol J. 2010; 10(4): 158-161. PMCID:PMC2847865.
16. Hakim A, Grahame R. Non-musculoskeletal symptoms in joint hypermobility syndrome. Indirect evidence for autonomic dysfunction? Rheumatology. Volume 43, Issue 9: 1194-1195.
17. Staud R. Autonomic dysfunction in fibromyalgia syndrome: postural orthostatic tachycardia. Curr Rheumatol Rep. 2008 December; 10(6):463-6. PMID 19007537.
18. Kanjwal K, Karabin B, Kanjwal Y, Grubb B. Autonomic dysfunction presenting as postural orthostatic tachycardia syndrome in patients with multiple sclerosis. Int J Med Sci. 2010; 7(2): 62-67. PMCID: PMC2840604.
19. Wang N., Orr0Urtreger A, Chapman J, Rabinowitz R, Korczyn A. Deficiency of Nicotinic Acetylcholine Receptor B4 Subunit Causes Autonomic Cardiac and Intestinal Dysfunction. Molecular Pharmacology. March 2003; vol 63, no. 3; 574-580.
20. Moreno D. Cognitive improvement in mild to moderate Alzheimer's dementia after treatment with the acetylcholine precursor choline alfoscerate: a multicenter, double-blind, randomized, placebo-controlled trial. Clin Ther 25(1): 178-93. PMID 12637119.
21. Parnetti, L; et al. Cholinergic precursors in the treatment of cognitive impairment of vascular origin: Ineffective approaches or need for re-evaluation? Journal of the Neurological Sciences 257 (1-2):264-9. PMID: 17331541.
22. White H L, Scates P W. Acetyl-L-Carnitine as a precursor of acetylcholine. Neurochem Res. 1990 June; 15(6):597-601. PMID: 2215852.
23. Gatti G, Barzaghi N, Acuto G, Abbiati G, Fossati T, Perucca E. A comparative study of free plasma choline levels following intramuscular administration of L-alpha-glycerylphosphorylcholine and citicoline in normal volunteers. Int J Clin Pharmacol Ther Toxicol. 1992 September; 30(9): 331-5. PMID: 1428296.
24. Kuratsune H, Yamaguti K, Takahashi M, et al. Acylcarnitine deficiency in chronic fatigue syndrome. Clin Infect Dis 1994; 18:S62-S67.
25. Plioplys A V, Plioplys S. Serum levels of carnitine in chronic fatigue syndrome: clinical correlates. Neuropsychobiology 1995; 32:132-138.
26. Virmani A, Koverech A, Ali S, Binienda Z. Acetyl-L-Carnitine modulates TP53 and IL10 gene expression induced by 3-NPA evoked toxicity in PC12 cells. Curr Neuropharmacol. 2011 March; 9(1): 195-199. PMCID: PMC3137180.
27. White H L, Scates P W. Acetyl-L-Carnitine as a precursor of acetylcholine. Neurochem Res. 1990 June; 15(6):597-601. PMID: 2215852.
28. Ho Y, So K, Chang R. Drug discovery from Chinese medicine against neurodegeneration in Alzheimer's and vascular dementia. Chin Med. 2011; 6:15. PMC3097009.
29. Peskind E R, Wingerson D,m Pascualy M, Thal L, Veith R C, Dorsa D M, Bodenheimer S, Raskind M A. Oral physostigmine in Alzheimer's disease: effects on norepinephrine and vasopressin in cerebrospinal fluid and plasma. Biol Psychiatry. 1995 Oct. 15; 38(8): 532-8. PMID 8562665.
30. Kanjwal K, Saeed B, Karabin B, Kanjwal Y, Grubb B P. Clinical presentation and management of patients with hyperadrenergic postural orthostatic tachycardia syndrome. A single center experience. Cardiol J. 2011; 18(5): 527-31. PMID 21947988.
31. Agarwal A, Garg R, Ritch A, Sarkar P. Postural orthostatic tachycardia syndrome. Postgrad Med J. 2007 July; 83(981): 478-480. PMCID: PMC2600095.
32. Faulkner J M. Nicotine poisoning by absorption through the skin. J Am Med Assoc 1993; 100: 1664-1665.
33. Nijs J, Aerts A, DeMeirleir K. Generalized joint hypermobility is more common in chronic fatigue syndrome than in healthy control subjects. Journal of Manipulative and Physiological Therapeutics. 29; 1, 2006: 32-39;[33]
34. Gibbons C H, Bonyhay I, Benson A, Wang N, Freeman R (2013) Structural and Functional Small Fiber Abnormalities in the Neuropathic Postural Tachycardia Syndrome. PLoS ONE 8(12): e84716
35. Busha B, Stella M, Manning H, Leiter J. Termination of inspiration by phase-dependent respiratory vagal feedback in awake normal humans. J Appl Physiol 93:903-910, 2002.
36. Zarate N, Farmer A, Grahame R, Mohammed S, Knowles C, Scott S, Aziz Q. Unexplained gastrointestinal symptoms 37. Driscoll D. The Driscoll Theory: Discovering the Cause of POTS in Ehlers-Danlos Syndrome. Warnick Publishing, 2012. Print
38. Houi K, Oka H, Mochio S. The effects of nicotine on a patient with spinocerebellar degeneration whose symptoms temporarily exacerbated by cigarette smoking Rinsho Shinkeigaku. 1993 July 33(7):774-6
39. Timothy C O. Effect of 0.5% glucose intake on the tear production of normoglycemic emmetropic Nigerians. JNOA Vol 15, 2009
40. Castori M, Ehlers-Danlos syndrome, hypermobility type: an underdiagnosed hereditary connective tissue disorder with mucocutaneous, articular, and systemic manifestations. Dermatol. 2012: 751768 PMC 3512326
41. Bennett R. Adult growth hormone deficiency in patients with fibromyalgia. Curr Rheumatol Rep. 2002 August; 4(4):306-12.
42. Cuatrecasas G, Alegre C, Fernandez-Sola J, Gonzalez M, Garcia-Fructuoso F, Poca-Dias V, et al. Growth hormone treatment for sustained pain reduction and improvement in quality of life in severe fibromyalgia. Pain. 2012 July; 153(7):1382-9.
43. Young P, Bicknell R, Schofield J. Acetylcholine stimulates growth hormone secretion, phosphatidyl inositol labelling, Ca+2 efflux and cyclic GMP accumulation in bovine anterior pituitary glands. Journal of Endocrinology. February 1979 80:203-213
44. Traviesa D. Magnesium deficiency: a possible cause of thiamine refractoriness in Wericke-Korsakoff encephalopathy. Journal of Neurology, Neurosurgery, and Psychiatry, 1974, 37, 959-962
45. Wank S A. Cholecystokinin receptors. Am J. Physiol. 1995 November; 269(5 Pt 1): G628-46. PMID7491953
46. Neural regulation of lacrimal gland secretory processes: Relevance in dry eye diseases. Progress in Retinal and Eye Research 28 (2009): 155-177. Dartt, 2009
47. Milewicz D, Reid A, Cecchi A. Vascular Ehlers-Danlos Syndrome: Exploring the Role of Inflammation in Arterial Disease. Circulation: Cardiovascular Genetics. 2014; 7:5-7
48. Bachofen V, Kuhn A, Suschek C. The role of nitric oxide. Rheumatology. 2006; 45:3:7-9
49. Anderson, Philip 0.; Knoben, James E.; Troutman, William G, eds., Handbook of Clinical Drug Data, Tenth Edition, McGraw-Hill, 2002
50. Pratt and Taylor, eds., Principles of Drug Action, Third Edition, Churchill Livingston, New York, 1990
51. Katzung, ed., Basic and Clinical Pharmacology, Ninth Edition, McGraw Hill, 2003
52. Goodman and Gilman, eds., The Pharmacological Basis of Therapeutics, Tenth Edition, McGraw Hill, 2001
53. Remington's Pharmaceutical Sciences, 20th Ed., Lippincott Williams & Wilkins., 2000
54. Martindale, The Extra Pharmacopoeia, Thirty-Second Edition (The Pharmaceutical Press, London, 1999)
55. Remington: The Science and Practice of Pharmacy, Pharmaceutical Press; 22nd Edition (2012)
56. Remington's Pharmaceutical Sciences, Mack Publishing Company
57. Zeisel S. Choline: Critical role during fetal development and dietary requirements in adults. Annu Rev Nutr. 2006; 26:229-250. PMCID:PMC2441939
58. Fischer L, daCosta K, Kwock L, Stewart P, Lu T, Stabler S, et al. Sex and menopausal status influence human dietary requirements for the nutrient choline. Am J Clin Nutr. 2007 May; 85(5):1275-1285. PMCID:PMC2435503
59. Molae V, Ibarzabal A, Sanchez B, Flores L, Angreu A, Lacy A, Vidal J. Nystagmus: an uncommon neurological manifestation of thiamine deficiency as a serious complication of sleeve gastrectomy. Nutr Clin Pract. 2012 December:27(6):788-92 PMID 23042832
60. Henderson, Faser, "Neurosurgical Problems with Ehlers-Danlos syndrome." Think Tank/The Coalition Against Pediatric Pain. Providence, R.I. Aug. 4, 2013. Lecture
61. Traviesa D. Magnesium deficiency: a possible cause of thiamine refractoriness in Wernicke-Korsakoff encephalopathy. Journal of Neurology, Neurosurgery, and Psychiatry, 1974, 37, 959-962
62. Craciunescu C, Zeisel S. Maternal dietary choline deficiency alters angiogenesis in fetal mouse hippocampus. PNAS July 2010; 107:29
63. Eccles J, Beacher F, Gray M, Jones C, Minati L, Harrison N, Critchley H. Brain structure and joint hypermobility: relevance to the expression of psychiatric symptoms. Br J Psychiatry. June 2012:200(6):508-509
64. Meck W, Smith R, Williams C. Pre- and postnatal choline supplementation produces long-term facilitation of spatial memory. Dev Psycholbiol. 1988 May; 21(4):339-53

What is claimed is:

1. A method of treating autonomic dysfunctions in a subject, comprising administering to a subject in need thereof an effective amount of a composition comprising a choline compound; a cholinesterase inhibitor and Acetyl-L-Carnitine in an amount effective to treat one or more of the following autonomic dysfunctions associated with collagen disorders: Ehlers-Danlos syndrome, Marfan's syndrome, Loeys-Dietz syndrome, Stickler syndrome, fibrillary disorders, elastin disorders, or Joint Hypermobility Syndrome.

2. The method of claim 1, wherein the composition treats or prevents symptoms associated with autonomic disorders including constipation, gastroparesis, idiopathic gastrointestinal dysmotility, low gastric acid production, ileocecal valve dysfunction ("ileus"), breathing difficulties, low gall bladder ejection fractions, biliary dyskinesia, acalculous gall bladder disease, Sphincter of Oddi dysfunction, low cholecystokinin ("CCK") production, poor kidney function, non-alcoholic steatohepatitis (or "NASH"), or non-alcoholic fatty liver disease.

3. The method of claim 1, wherein the composition comprises:
   a choline compound selected from at least one of choline at 100 mg to 1,000 mg, lecithin at 100 mg to 3 grams, or L-alpha glycerylphosphorylcholine at 30 mg to 2,400 mg;
   75 mcg to 300 mcg of a cholinesterase inhibitor is huperzine A; and
   50 mg to 600 mg of Acetyl-L-Carnitine.

4. The method of claim 1, wherein the composition further comprises Thiamin.

5. The method of claim 1, wherein the composition further comprises Magnesium.

6. The method of claim 1, wherein the composition comprises per dose:
   a choline compound selected from at least one of choline at 100 mg to 3,000 mg, lecithin at 100 mg to 3 grams, or L-alpha glycerylphosphorylcholine at 30 mg to 2,400 mg;
   75 mcg of huperzine A;
   150 mg of Acetyl-L-Carnitine; and
   optionally 30 mg Thiamin and 30 mg Magnesium.

7. The method of claim 1, wherein the range per dose is 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300 mg, of the choline compound.

8. The method of claim 1, wherein the range per dose is 75, 80, 90, 100, 125, 150, 175, 200, 225, 250, 275, 300, 75 to 300, 80 to 275, 90 to 250, 100 to 225, 125 to 200, 150 to 175 micrograms of huperzine A.

9. The method of claim 1, wherein the range per dose is 50, 75, 80, 90, 100, 125, 150, 175, 200, 225, 250, 275, 300, 325, 350, 375, 400, 425, 450, 475, 500, 525, 550, 575, 600, 50 to 600, 75 to 600, 80 to 575, 90 to 550, 100 to 525, 125 to 500, 150 to 475, 175 to 450, 200 to 425, 225 to 400, 250 to 375, 275 to 350, 300 to 325 mg Acetyl-L-Carnitine.

10. The method of claim 4, wherein the range per dose is 10, 20, 30, 40, 50, 60 mg Thiamin.

11. The method of claim 5, wherein the range per dose is 0.3, 0.5, 0.75, 1.0, 5, 10, 15, 20, 25, 30, 40, 50, 60, 70, 80, 90, 100 mg Magnesium.

12. The method of claim 1, wherein the composition is adapted to be administered prenatally, orally, intravenously, intraperitoneally, intranasally, intrapulmonary, subcutaneously, intracutaneously, or intramuscularly.

* * * * *